US011815098B1

(12) United States Patent
Patil et al.

(10) Patent No.: US 11,815,098 B1
(45) Date of Patent: Nov. 14, 2023

(54) PORTABLE AND WEARABLE COOLING AND HEATING DEVICE

(71) Applicants: Veersinh Patil, Malden, MA (US); Vinny Aswani, Boston, MA (US)

(72) Inventors: Veersinh Patil, Malden, MA (US); Vinny Aswani, Boston, MA (US)

( * ) Notice: Subject to any disclaimer, the term of this patent is extended or adjusted under 35 U.S.C. 154(b) by 0 days.

(21) Appl. No.: 17/961,628

(22) Filed: Oct. 7, 2022

(51) Int. Cl.
*F04D 25/08* (2006.01)
*F25B 21/02* (2006.01)
*A61F 7/00* (2006.01)

(52) U.S. Cl.
CPC .............. *F04D 25/08* (2013.01); *F25B 21/02* (2013.01); *A61F 2007/0011* (2013.01); *F04D 25/084* (2013.01)

(58) Field of Classification Search
CPC ........ F04D 25/08; F04D 25/084; F25B 21/02; A61F 2007/0011
See application file for complete search history.

(56) References Cited

U.S. PATENT DOCUMENTS

| 4,576,169 | A | 3/1986 | Williams |
| 7,892,306 | B2 | 2/2011 | Kummer et al. |
| 11,187,241 | B1 | 7/2021 | Liu et al. |
| 2008/0300529 | A1 | 12/2008 | Reinstein |
| 2009/0118869 | A1 | 5/2009 | Cauchy et al. |
| 2010/0198322 | A1 | 8/2010 | Joseph et al. |
| 2018/0064574 | A1* | 3/2018 | Adair ................ A61F 7/02 |
| 2021/0368872 | A1* | 12/2021 | Lee .................. F04D 25/084 |
| 2022/0235786 | A1* | 7/2022 | Liu ................... F04D 29/281 |

FOREIGN PATENT DOCUMENTS

| CN | 210531205 U | 10/2019 |
| EP | 2356340 B1 | 11/2009 |
| JP | 3220810 U | 1/2019 |
| KR | 102316736 B1 | 4/2020 |
| RU | 2567345 C2 | 2/2009 |

* cited by examiner

*Primary Examiner* — Michael C Zarroli
(74) *Attorney, Agent, or Firm* — Bay State IP, LLC

(57) ABSTRACT

Certain aspects are directed to a portable and wearable cooling and heating device configured to regulate temperature by blowing cool or warm air that is transferrable, light weight, flexible, and retractable. The device comprises a first support arm, a second support arm, and a control module that is preferably battery powered configured to control the speed of air flow. The first and second support arm each further comprises an air canal with a plurality of air outlets, temperature packs, insulation pads, a housing configured to receive an air flow supplier, an air flow supplier nozzle that directs and enhances the air flow, an air flow barrier that prevents air from reentering the air flow supplier. Additionally, the first and second support arms of the wearable cooling and heating device are further provided with at least one Peltier device to optimize the air temperature and an aromatherapy chamber.

19 Claims, 28 Drawing Sheets

PORTABLE AND WEARABLE COOLING AND HEATING DEVICE

BACKGROUND OF THE INVENTION

Field of the Invention

This disclosure relates generally to a cooling and heating device designed to regulate temperature for comfort. More particularly, the present disclosure relates to a portable and wearable temperature regulating device preferably configured to be worn on a user's body to assist in cooling and heating.

Description of the Related Art

During nice weather and especially during the warmer summer months people, along with their pets, enjoying spending time outdoors and partaking in numerous outdoor activities. However, it is important and desirable during these outdoor activities to maintain a relatively normal body temperature to avoid heat exhaustion or heat stroke especially during strenuous activities.

There are numerous ways one can attempt to stay cool and avoid elevated body temperature during outdoor activities in the heat including carrying a personal fan, drinking plenty of cold fluids, sitting the shade or walking through a misting station. During visits to amusement parks, sporting events or summer concerts, attempts are made to help the crowd stay cool, but too often the temperature is either too cool or not cool enough, leaving individuals uncomfortable and without the ability to find the perfect environment for themselves.

Additionally, pet owners need to make sure that animals are taken care of during these warmer days as they are especially vulnerable to the heat. Again, solutions such as applying a cool towel or jumping in a pool or cold body of water may provide temporary reprieve to warm temperatures. Whether an individual or their pet, people have been looking for convenient and relatively easy solutions to beat the heat and stay cool while being able to enjoy outdoor activities.

SUMMARY OF THE INVENTION

The present device, as illustrated herein, is clearly not anticipated, rendered obvious, or even present in any of the prior art, either alone or in any combination thereof. Thus, the several embodiments of the present device are illustrated herein.

A primary object of the present disclosure is a portable and wearable cooling and heating device configured to regulate temperature for comfort by blowing cool or warm air that is easily transferrable, light weight, and flexible. The device is configured to maintain optimal air temperature for both humans and pets and can be worn on different body parts.

Accordingly, certain aspects are directed to a portable and wearable cooling and heating device, wherein the device comprises a first support arm, a second support arm, and a control module that is preferably battery powered configured to control the speed of air flow. The first and second support arms each further comprises an air canal with a plurality of air outlets, temperature packs to cool or warm the air flow, insulation pads, a housing configured to receive an air flow supplier, an air flow supplier nozzle that directs and enhances the air flow, an air flow barrier that prevents air from re-entering the air flow supplier, and at least one Peltier device to optimize the air temperature.

In one embodiment, the portable and wearable cooling and heating device also includes a plurality of fans to generate forced air, a plurality of air outlets along the length of the support arms, a plurality of top, middle bottom, and bottom heat sinks inside the support arms, and thermistors disposed on the heat sinks and the Peltier device to monitor and control the temperature inside the air canals.

Other embodiments also include an aromatherapy chamber designed to receive a mesh and a plurality of diffuser pads/sponges that can release different scent into the air through the aromatherapy chamber outlets to make a pet's clothing smell fresh and may also function as a stress reliever.

In some embodiments, the portable and wearable cooling and heating device further comprises several vent covers, including a top vent cover and vent covers for the support arms to release heat generated by the device.

In yet another embodiment, the portable and wearable cooling and heating device is equipped with vapor chambers disposed underneath the top heat sinks which allows heat to be released and absorbed quickly.

One embodiment of the portable and wearable cooling and heating device has retractable support arms and others are connected by flexible connectors made of durable fabrics or plastic composite such that the device may accommodate different body part sizes and needs.

There has thus been outlined, rather broadly, the more important features of the portable and wearable cooling and heating device, in order that the detailed description thereof that follows may be better understood, and in order that the present contribution to the art may be better appreciated. There are additional features of the device that will be described hereinafter and which will form the subject matter of the claims appended hereto.

In this respect, before explaining at least one embodiment of the system in detail, it is to be understood that the device is not limited in its application to the details of construction and to the arrangements of the components set forth in the following description, and/or illustrated in the drawings. The device is capable of other embodiments and of being practiced and carried out in various ways. Also, it is to be understood that the phraseology and terminology employed herein are for the purpose of description and should not be regarded as limiting.

These together with other objects of the device, along with the various features of novelty, which characterize the device, are pointed out with particularity in the claims annexed to and forming a part of this disclosure. For a better understanding of the device, its operating advantages and the specific objects attained by its uses, reference should be made to the accompanying drawings and descriptive matter in which there are illustrated preferred embodiments of the system.

The foregoing has outlined the more pertinent and important features of the device in order that the detailed description of the device that follows may be better understood, and the present contributions to the art may be more fully appreciated. It is of course not possible to describe every conceivable combination of components, but one of ordinary skill in the art may recognize that many further combinations or permutations are possible. Accordingly, the novel structural components described below is intended to embrace all such alterations, modifications, and variations that fall within the spirit and scope of the appended claims.

DETAILED DESCRIPTION OF THE SEVERAL EMBODIMENTS

Figure 1A:
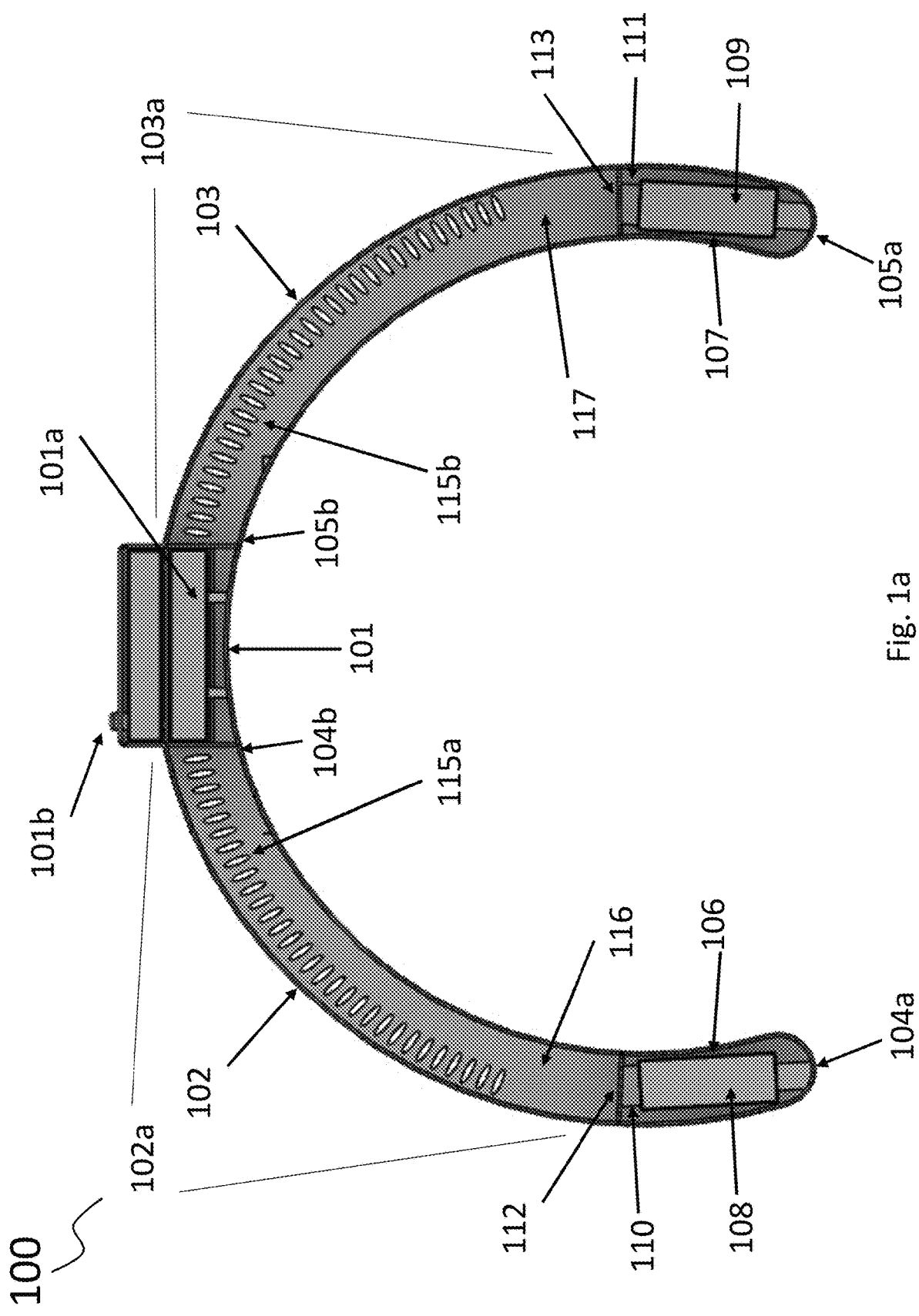
FIG. 1a illustrates a schematic diagram showing a front view of the wearable cooling and heating device.

Reference will now be made to non-limiting embodiments, examples of which are illustrated in the Figures. In one embodiment of a wearable cooling and heating device 100 as illustrated in FIG. 1a, the wearable cooling and heating device 100 comprises a first support arm 102 and a second support arm 103, wherein the first and the second support arms 102, 103 are preferably curved such that they can rest along a circumference of the neck of a human being or a pet comfortably. In addition, the wearable cooling and heating device 100 is preferably powered by a portable power source 101a located inside a control module 101, wherein an air speed is controlled by a control panel 101b.

In one embodiment, the control module 101, the first support arm 102, and the second support arm 103 are removably connected. The first support arm 102 further comprises a first group of air outlets 115a located along a circumference 102a of the first support arm 102 and a first housing 106 near a first distal end 104a. The second support arm 103 further comprises a second group of air outlets 115b located along a circumference 103a of the second support arm 103 and a second housing 107 near a second distal end 105a. A first proximal end 104b of the first support arm 102, the control module 101, and a second proximal end 105b of the second support arm 103 are connected together to form the wearable cooling and heating device 100. The first housing 106 and the second housing 107 are configured to receive first air flow supplier 108 and second air flow supplier 109 respectively designed to increase the air speed. The first air flow supplier nozzle 110 is attached to the first air flow supplier 108, and the second air flow supplier nozzle 111 is attached to the second air flow supplier 109. The first and second air flow supplier nozzles 110, 111 are designed to streamline and direct air flow into a first air canal 116 and a second air canal 117 respectively.

Specifically, the first and second air canal 116, 117 possess hollow space which allows air to travel from the first and second air flow supplier 108, 109 via the first and second air flow supplier nozzle 110, 111 through the first and second groups of air outlets 115a, 115b.

In order to prevent air that has already entered the first air canal 116 and the second air canal 117 from reentering the air flow suppliers 108, 109, the first air flow supplier nozzle 110 is fitted with a first air flow barrier 112, and the second air flow supplier nozzle 111 is fitted with a second air flow barrier 113. The first and second air flow barriers 112, 113 are provided to increase an efficiency to condition new air by avoiding reprocessing air.

Figure 1B:
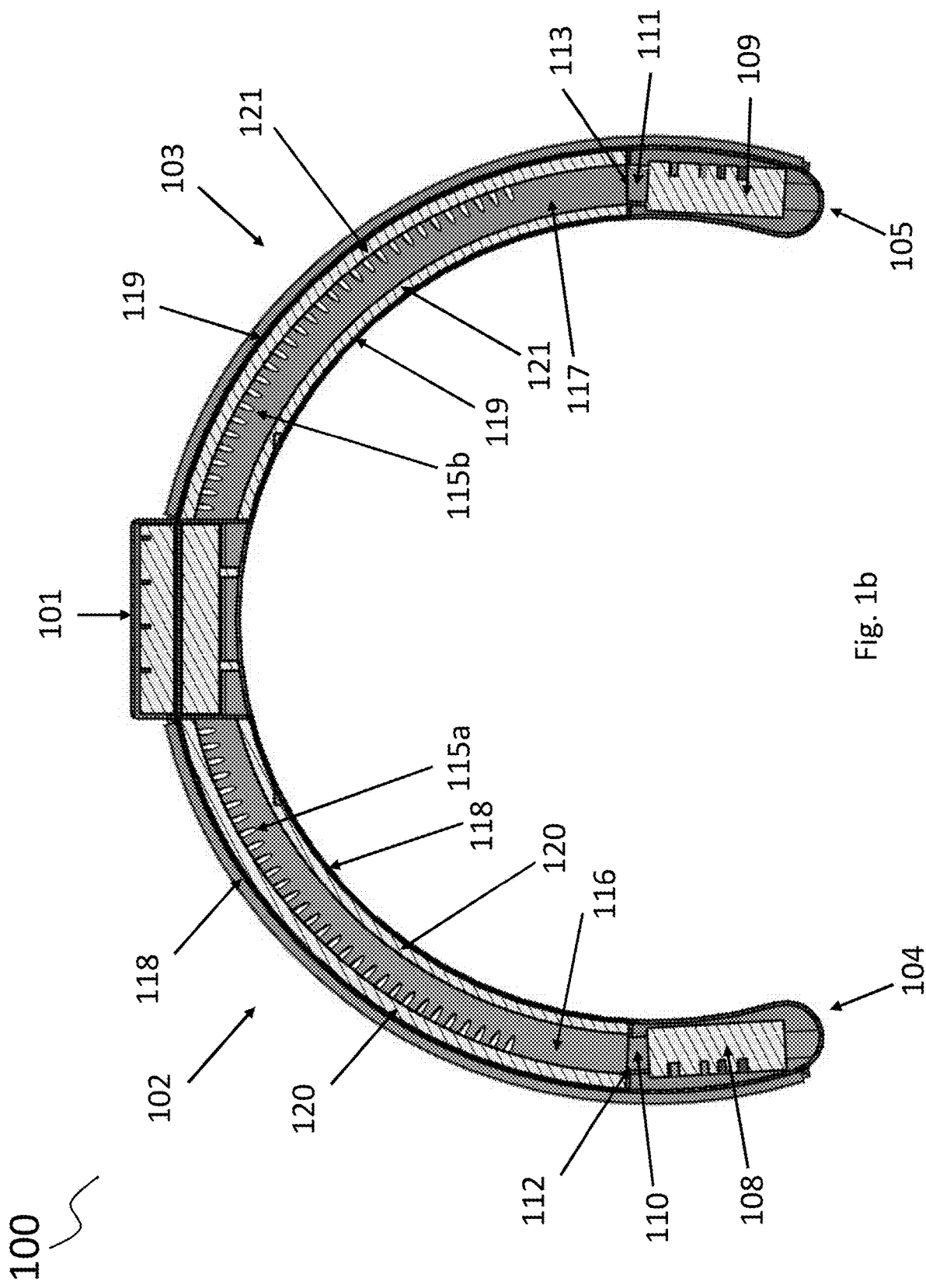
FIG. 1b illustrates a schematic diagram showing a cross-sectional view of the wearable cooling and heating device.

As illustrated in FIG. 1b, in a preferred embodiment, the first support arm 102 of the wearable cooling and heating device 100 comprises a first insulation pad 118 and a first temperature pack 120, wherein the first temperature pack 120 is located between the first insulation pad 118 and the first air canal 116. The second support arm 103 further comprises a second insulation pad 119 and a second temperature pack 121, wherein the second temperature pack 121 is located between the second insulation pad 119 and the second air canal 117.

The first and second temperature packs 120, 121 are reusable and removable packs with cooling and/or heating agent. When air is blowed from the first and the second air supplier nozzles 110, 111 into the air canals 116, 117, the temperature of the air flowing through the temperature packs 120, 121 is manipulated depending on the treatment conducted by the temperature packs 120, 121. Air flows through the air canals 116, 117 which allows it to be exposed to the surrounding temperature resulting in a change to the air temperature prior to exiting through the first and second groups of air outlets 115a, 115b. The first and the second air flow supplier nozzles 112, 113 are aligned with the first and the second temperature packs 120, 121 to ensure that most of the air flows through the temperature packs 120, 121 in order to reach a desirable temperature. When the performance of the temperature packs 120, 121 degrade over time, a user may replace the temperature packs to ensure proper cooling and heating.

Figure 2:
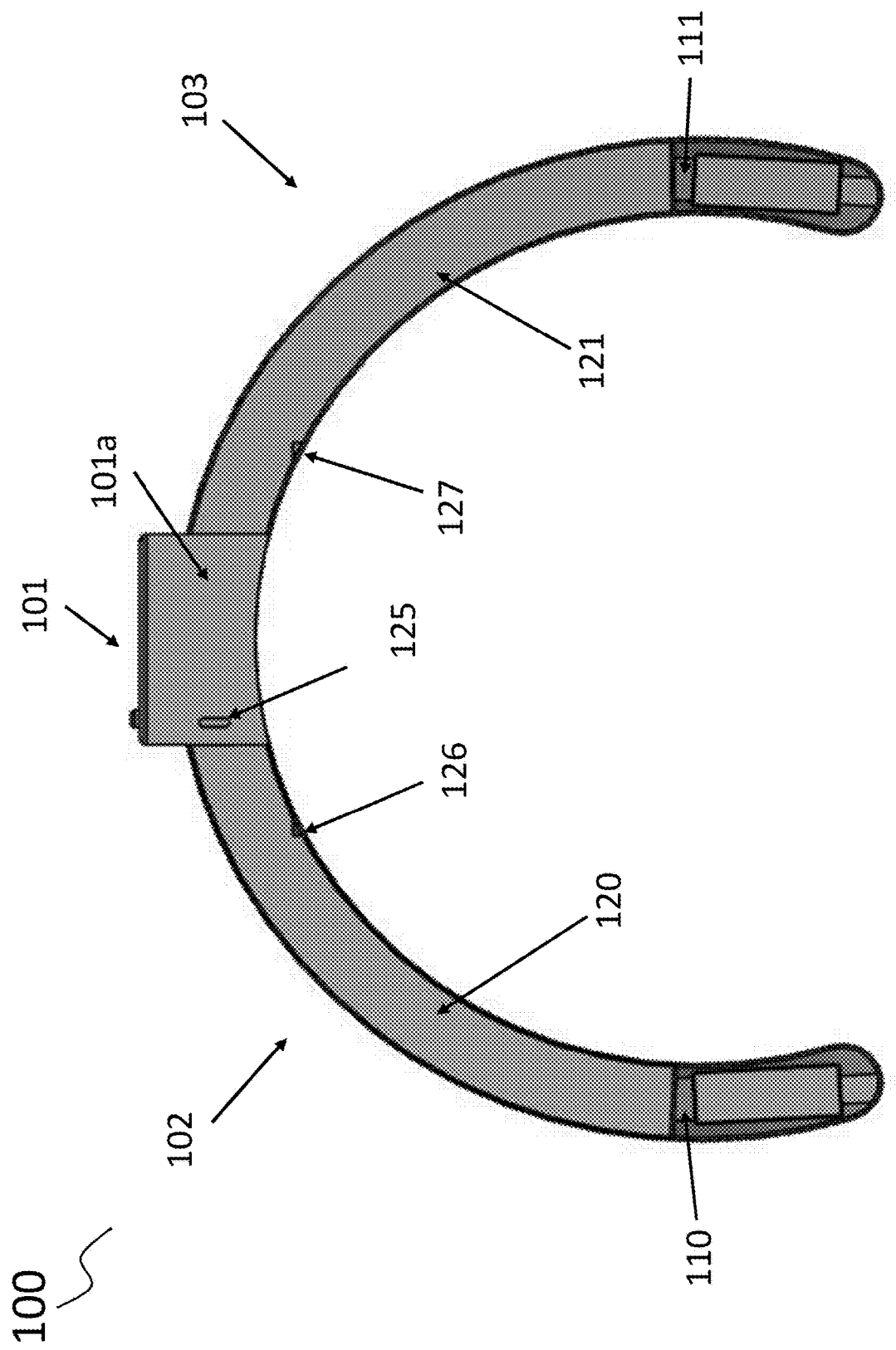
FIG. 2 illustrates a schematic diagram showing a back view of the wearable cooling and heating device.

A back view of the preferred embodiment of the wearable cooling and heating device 100 is illustrated in FIG. 2. The control module 101 further comprises a charging port 125, which is preferably a USB type A, B, or C charging port configured to charge the power source 101a.

Figure 3:
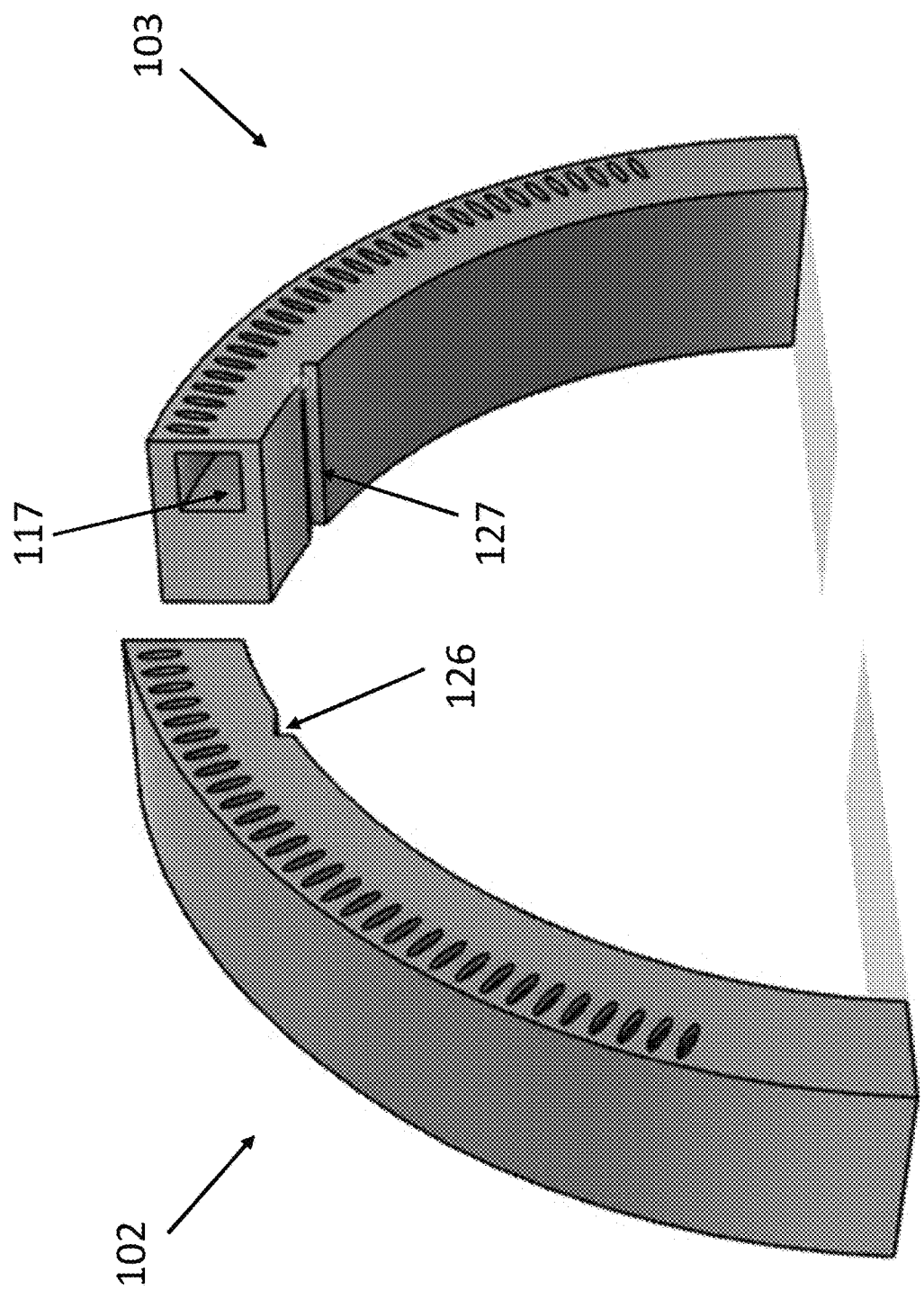
FIG. 3 illustrates a schematic diagram showing a perspective view of a first support arm and a second support arm of the wearable cooling and heating device.
Figure 4:
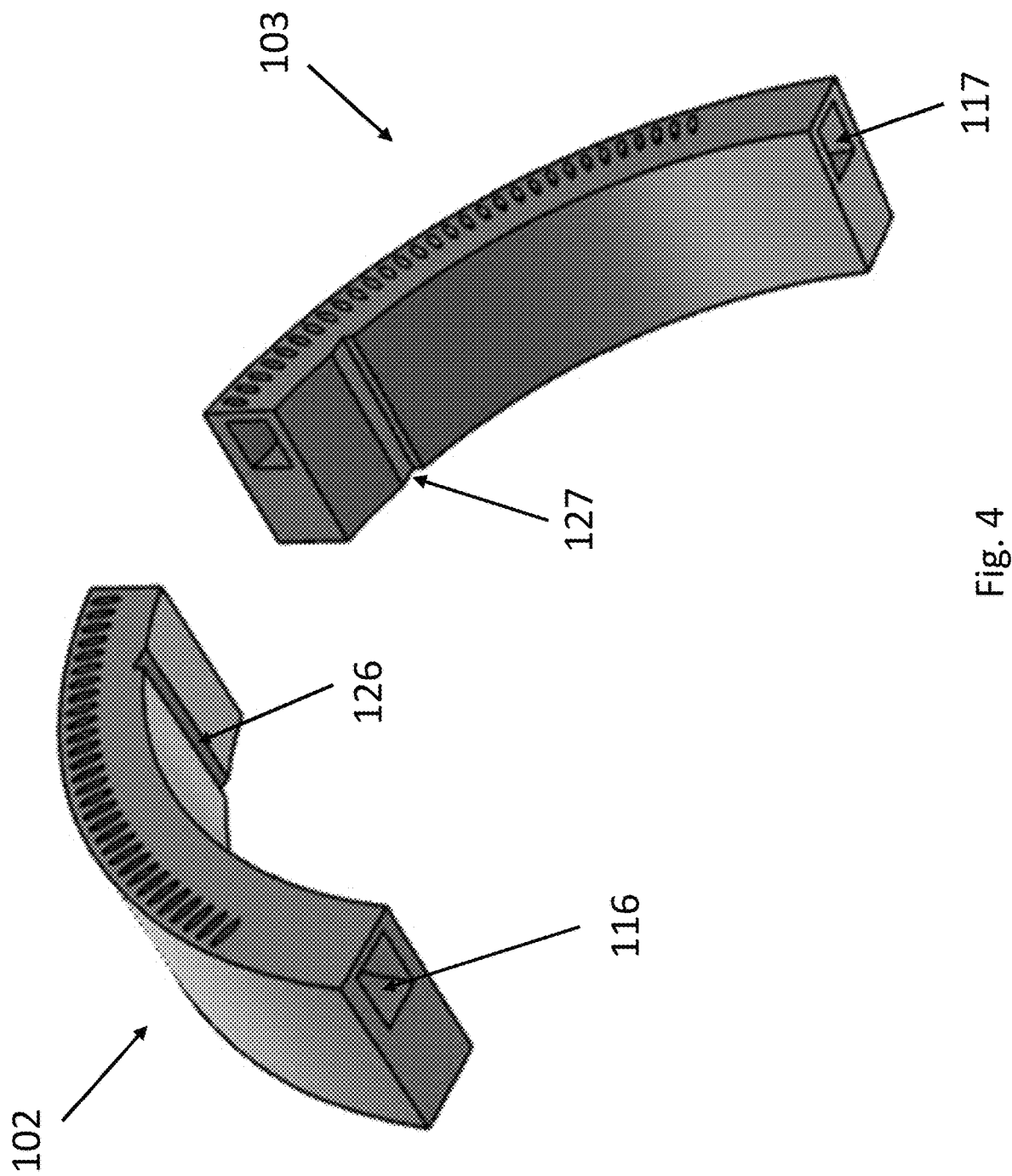
FIG. 4 illustrates a schematic diagram showing a bottom perspective view of air canals inside the first and the second support arms.

In addition, the first and the second support arms 102, 103 are preferably provided with a first alignment notch 126 and a second alignment notch 127 respectively. The first and the second alignment notches 126, 127 are designed to ensure proper insertion of the temperature packs 120, 121 into the first and the second support arms 102, 103. The first and the second alignment notches 126, 127 are preferably located under the first and a second air canals 116, 117 near the control module 101 as illustrated in FIGS. 2-4. The first and the second air flow supplier nozzles 110, 111 connect the first and second air canals 116, 117 with the first and second air suppliers 108, 109 to enhance and direct air flow.

Figure 5:
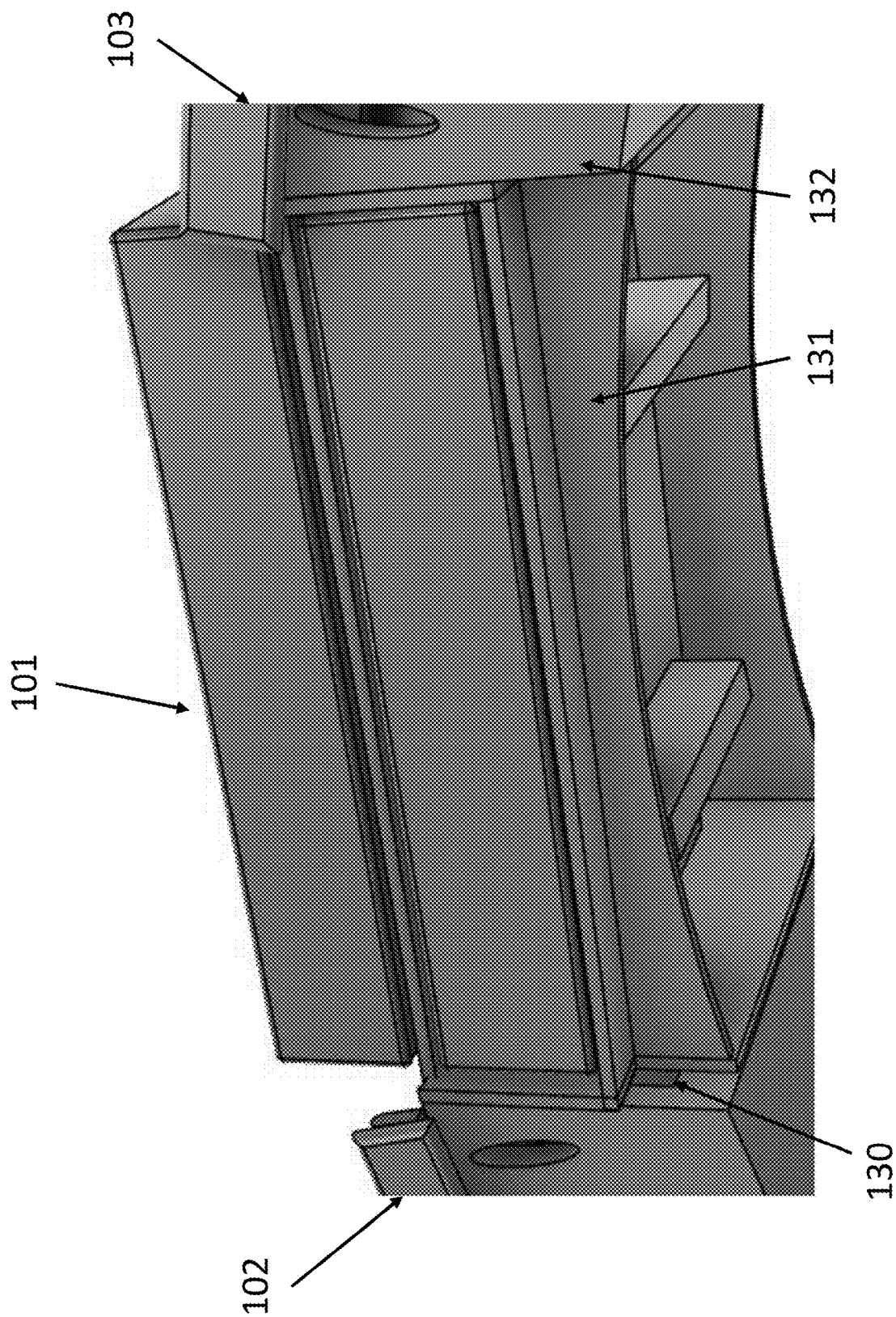
FIG. 5 illustrates a schematic diagram showing a perspective view of a control box and a front center air barrier of the wearable cooling and heating device.

In one embodiment as illustrated in FIG. 5, the first support arm 102 has a first canal exit 130, and the second support arm 103 has a second canal exit 132, wherein the first and second canal exits 130, 132 are provided to let any residue air escape from the first and second air canals 116, 117. Further, a front center air barrier 131 is provided under the control module 101 configured to control air flow from the first and the second canal exits 130, 132.

Figure 6:
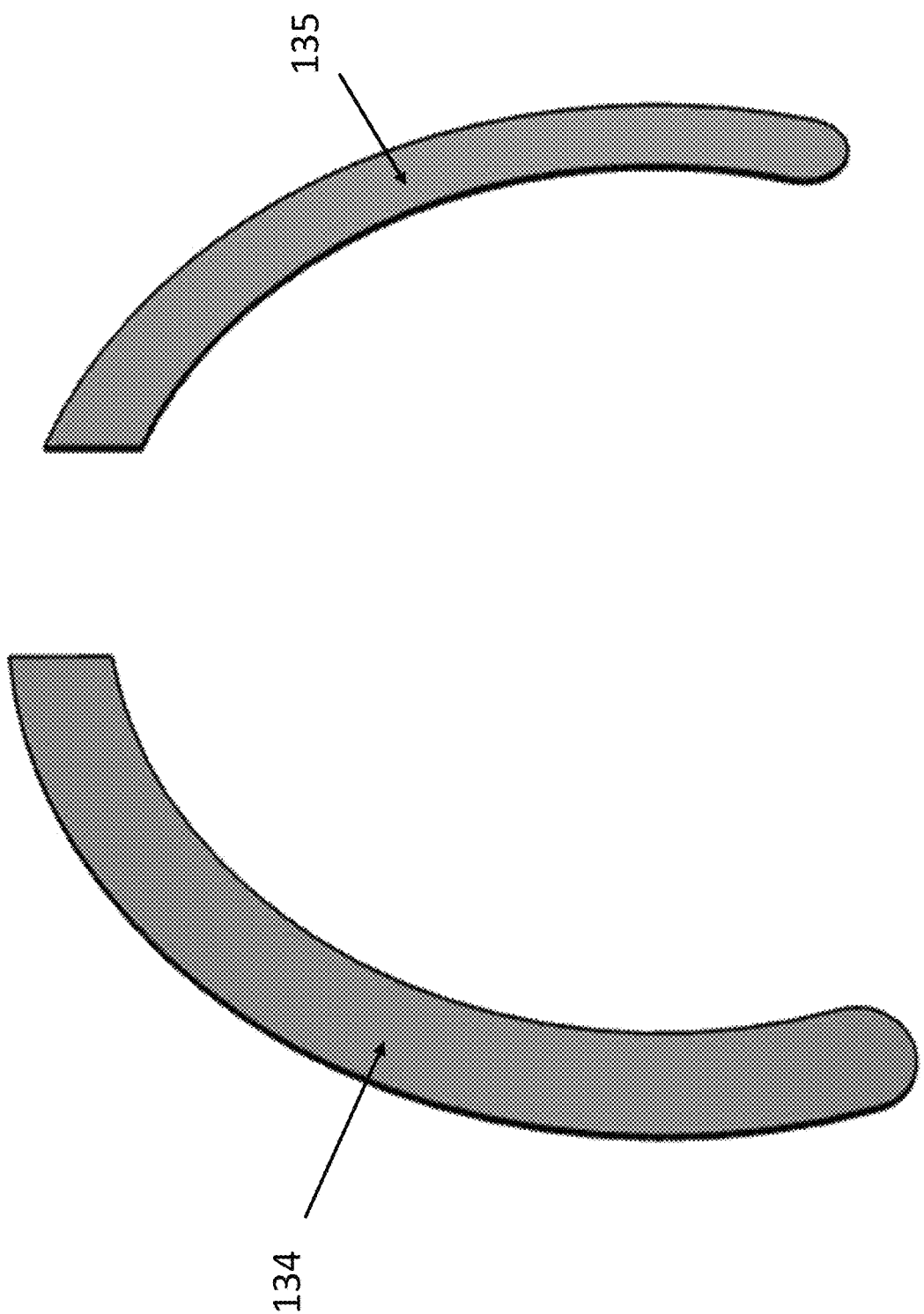
FIG. 6 illustrates a schematic diagram showing a perspective view of a first and a second removable back cover of the first and the second support arms.

FIG. 6 illustrates a schematic diagram showing a perspective view of a first removable back cover 134 of the first support arm 102 and a second removable back cover 135 of the second support arm 103. A user may remove the back covers 134, 135 to access and replace the temperature packs 120, 121.

Figure 7:
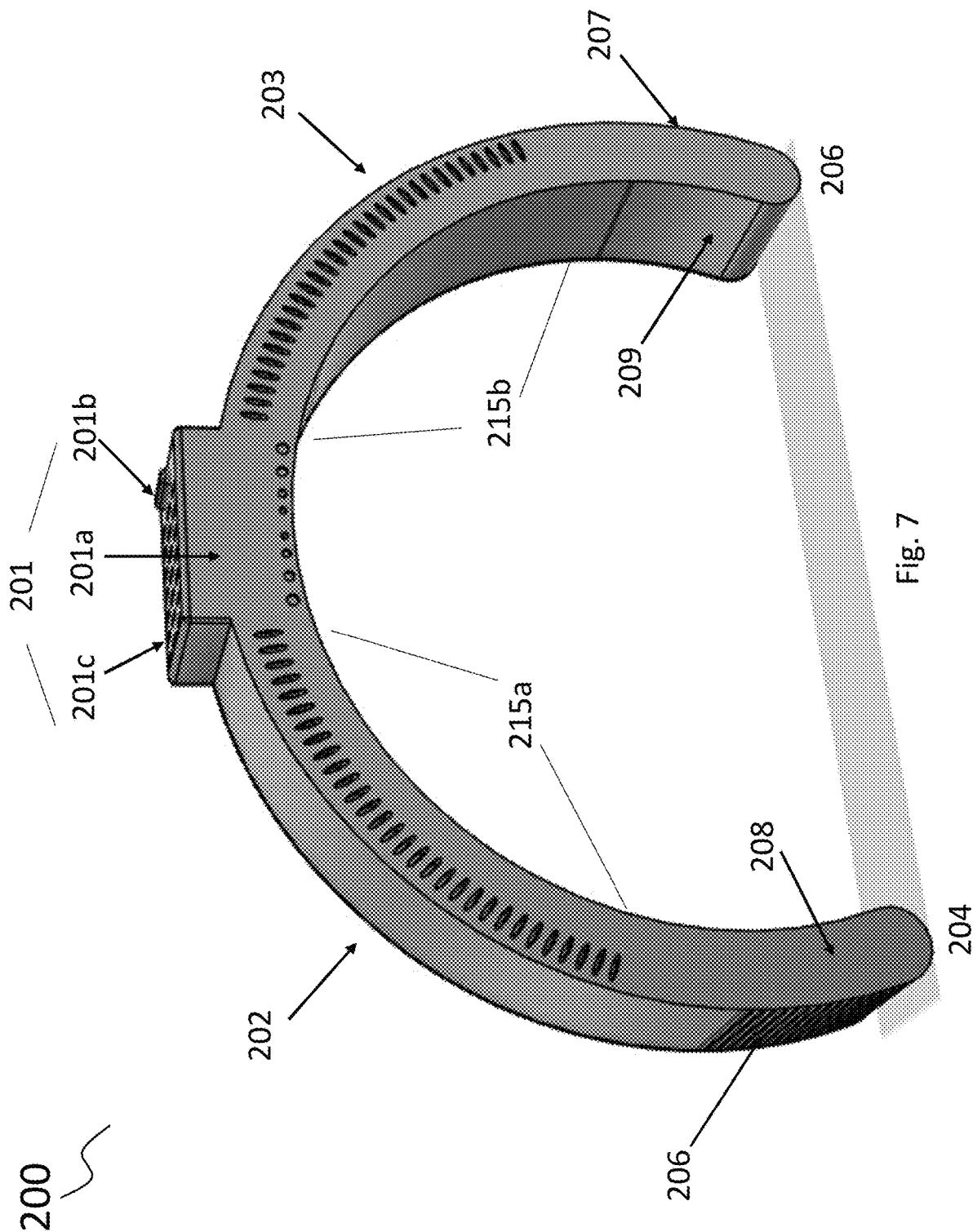
FIG. 7 illustrates a schematic diagram showing a perspective view of another embodiment of the wearable cooling and heating device.

In some embodiments as illustrated in FIG. 7, a wearable cooling and heating device 200 comprises a control module 201 connected to a first support arm 202 and a second support arm 203, wherein the first support arm 202 and the second support arm 203 are curved such that the wearable cooling and hearing device 200 may rest on a human or pet's neck comfortably. The control module 201 further comprises a power source 201a inside the control module 201, a vent cover 201c at the top of the control box 201, and a control switch 201b on the vent cover 201c. The vent cover 201c allows heat produced by the control module 201 to escape such that the wearable cooling and heating device 200 does not overheat and malfunction when used over a substantial period of time.

Additionally, a first and a second air flow inlets 206, 207 are provided near a first end 204 and a second end 206 respectively. Outside air is drawn into a first air flow supplier 208 and a second air flow supplier 209 via the first and the second air flow inlets 206, 207 for cooling and heating processes. The processed air is then released through air outlets 215a, 215b located along the first and the second support arms 202, 203.

Figure 8A:
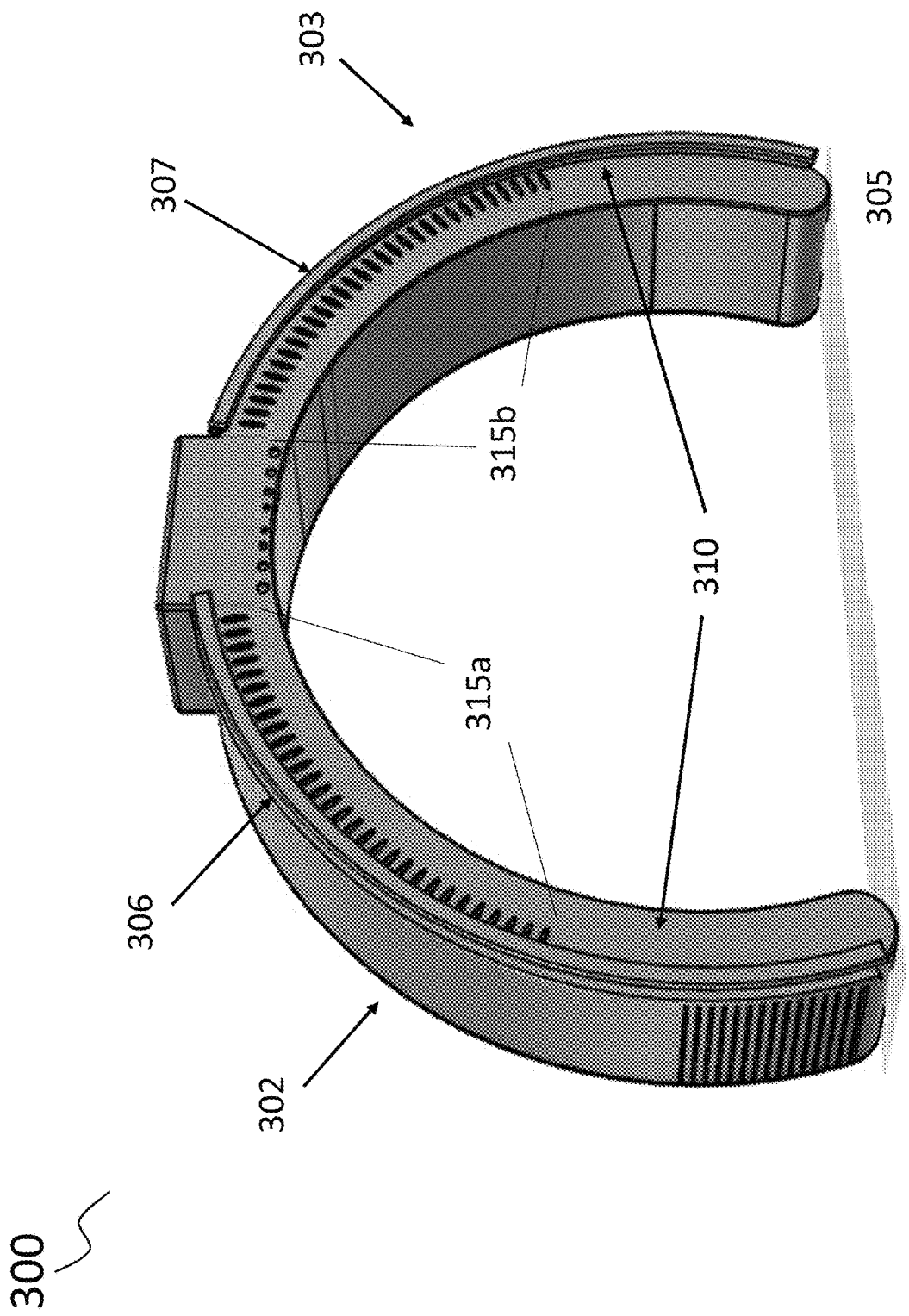
FIG. 8a illustrates a schematic diagram showing a perspective view of a wearable cooling and heating device with a pet recovery cone attachment.
Figure 8B:
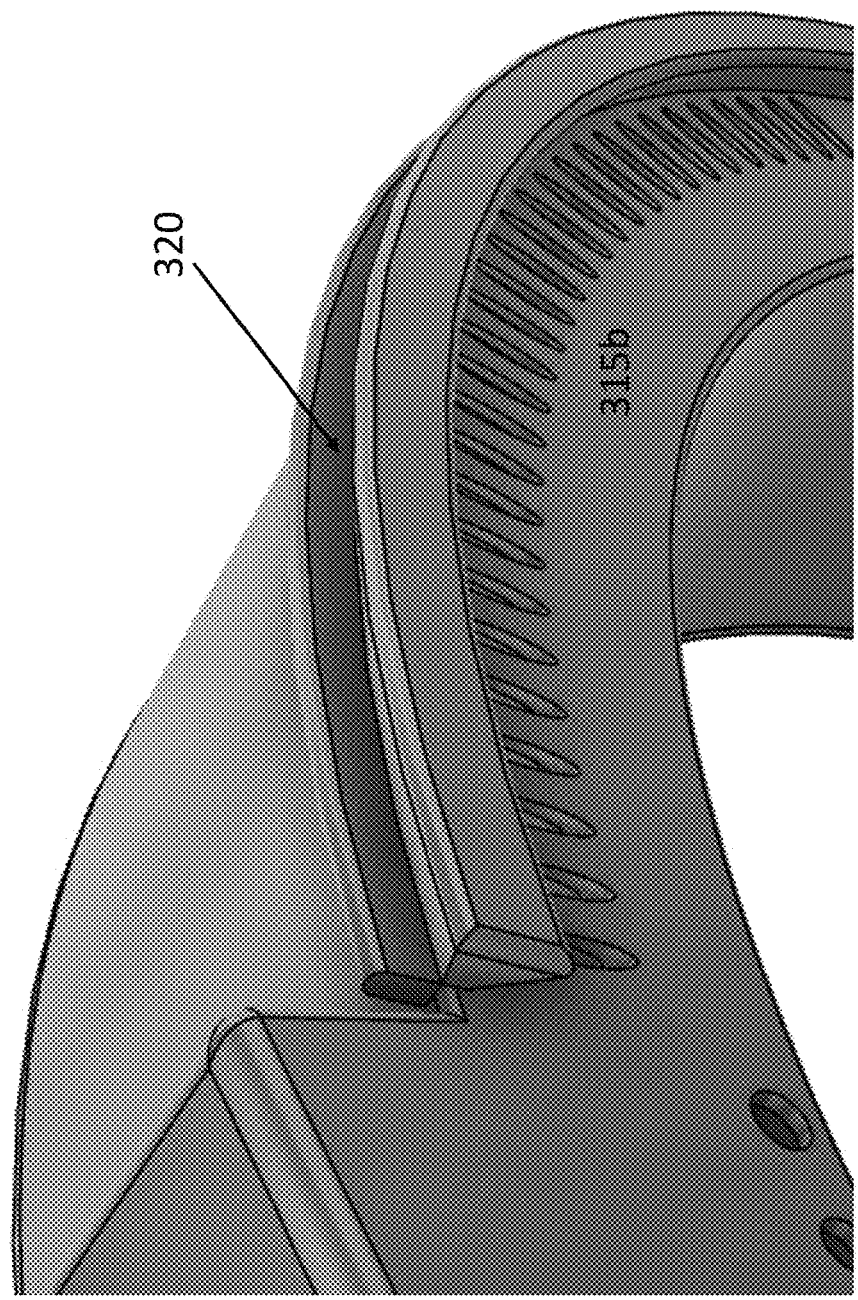
FIG. 8b illustrates a schematic diagram showing a perspective view of the pet recovery cone attachment.

In another embodiment of a wearable cooling and heating device 300 for pets as illustrated in FIGS. 8a and 8b, a first support arm 302 and a second support arm 303 of the wearable cooling and heating device 300 further comprises a first cone receiver 306 and a second cone receiver 307. The first and the second cone receivers 306, 307 are preferably extended from a front side 310 of the wearable cooling and heating device 300 along a full length of the first and second support arms 302, 303 such that a pet can wear the cooling and heating device 300 and a recovery cone around its neck at the same time.

In one embodiment, both the first and the second cone receivers 306, 307 have continuous grooves 320 along the length of each cone receiver as illustrated in FIG. 8b configured to guide and receive one end of a recovery cone.

Figure 9:
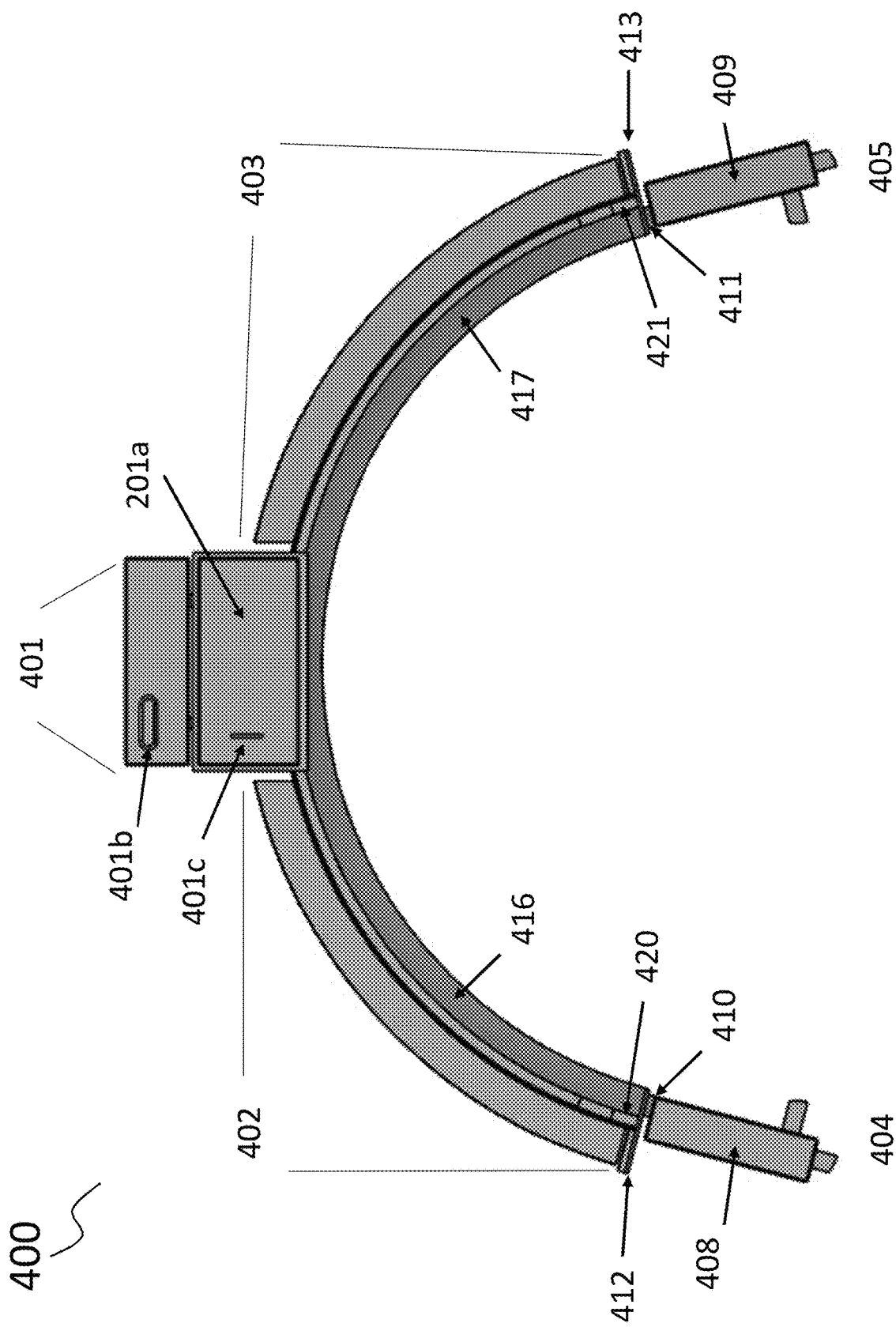
FIG. 9 illustrates a schematic diagram showing a back view of a wearable cooling and heating device with a Peltier device.

In another embodiment as illustrated in FIG. 9, a wearable cooling and heating device 400 utilizes a first Peltier device 420 and a second Peltier device 421 to increase or decrease air temperatures. The first and second Peltier devices 420, 421 are respectively located near a first air flow supplier nozzle 410 and a second air flow supplier nozzle 411. A first air flow supplier 408 near a first end of a first support arm 402 and a second air flow supplier 409 near a second end 405 of a second support arm 403 are designed to increase the speed of air. The first and second air flow suppliers 408, 409 are respectively fitted with the first air flow supplier nozzle 410 and the second air flow supplier nozzle 411 to direct air flow through a first air canal 416 and a second air canal 417 temperature controlled by the first and the second Peltier devices 420, 421. In addition, the wearable cooling and heating device 400 is preferably provided with a first air flow barrier 412 and a second air flow barrier 413 which stop air that has already entered the first and second air canals 416, 417 from reentering the air flow suppliers 408, 409.

Figure 10:
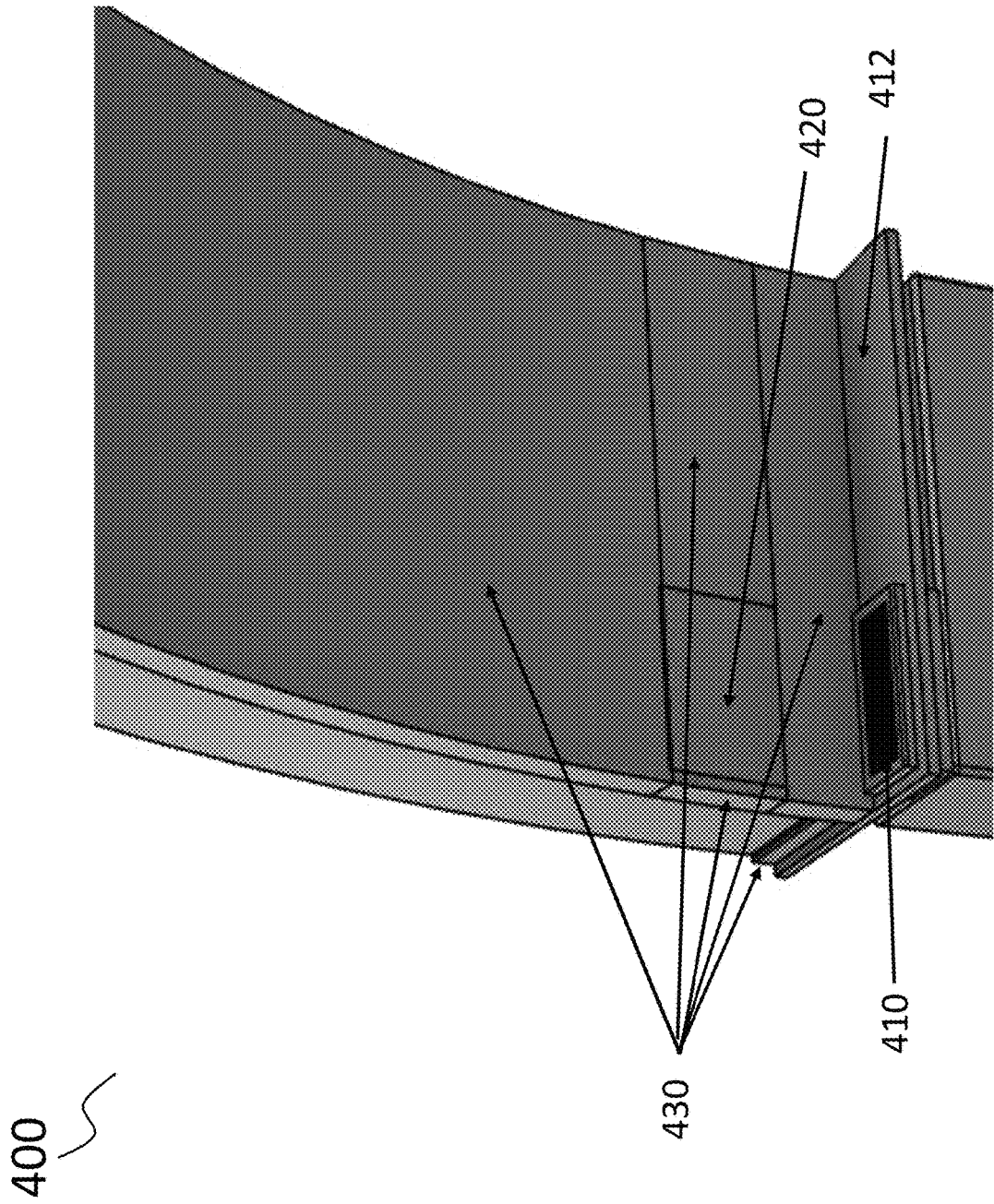
FIG. 10 illustrates a schematic diagram showing a perspective view of a plurality of insulation pads and the Peltier device in the wearable cooling and heating device.

In some embodiments as illustrated in FIG. 10, the wearable cooling and heating device 400 is equipped with a plurality of insulation pads 430 around the Peltier device 420. The Peltier device 420 and the adjacent air flow supplier nozzle 410 function collectively to manipulate the air temperature as it travels through the wearable cooling and heating device 400.

Figure 11:
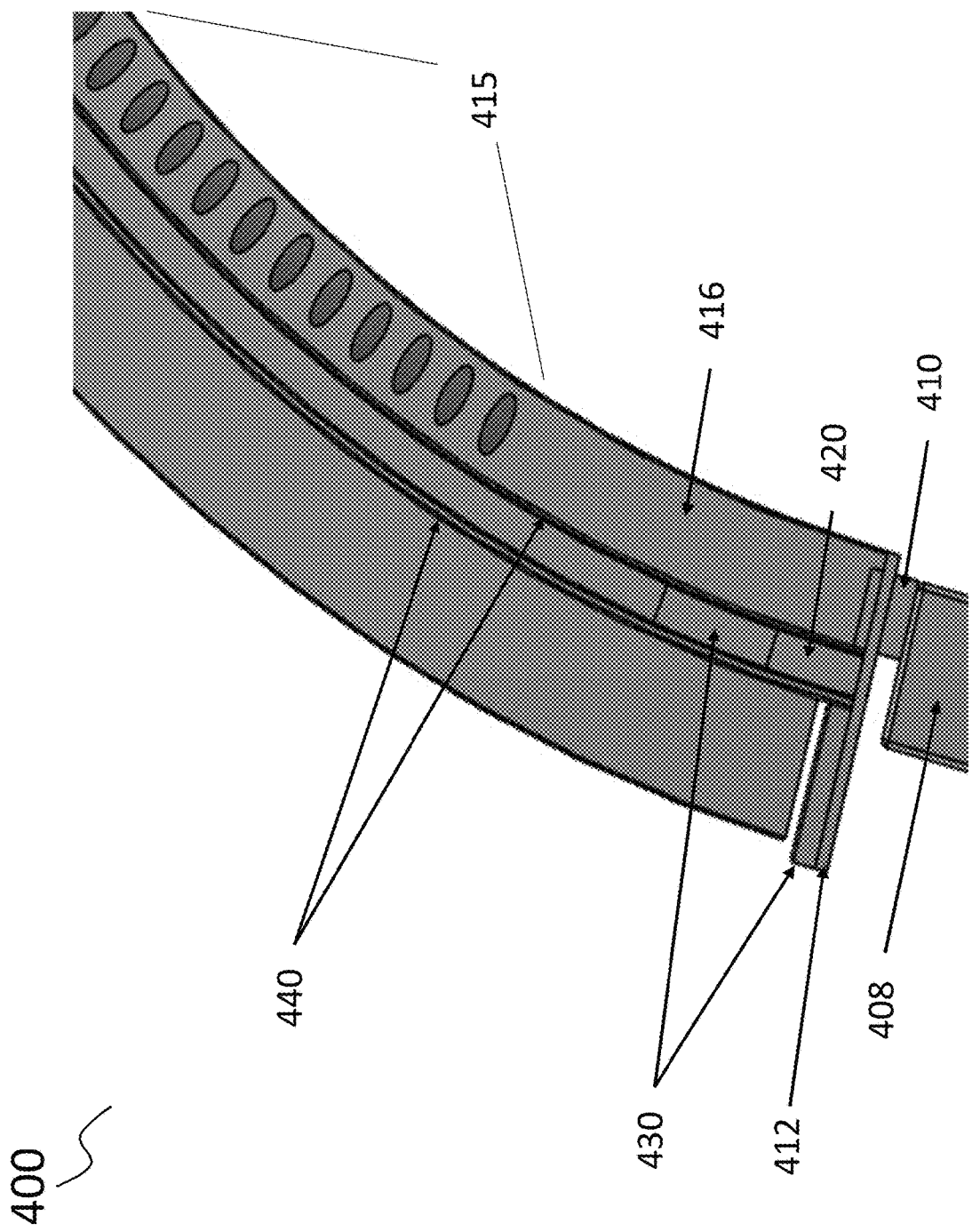
FIG. 11 illustrates a schematic diagram showing a side view of heat sink plates and the insulation pad in the wearable cooling and heating device with a Peltier device.

In a preferred embodiment as illustrated in FIG. 11, the wearable cooling and heating device 400 further comprises a plurality of heat sink plates 440, wherein the Peltier device 420 is located in between the plurality of heat sink plates 440 to make direct contact with the heat sink plates 440.

Additionally, the plurality of insulation pads 430 are provided behind the air flow barrier and in between the plurality of heat sink plates 440 next to the Peltier device 420 to seal the processed air from escaping or reentering the air flow supplier 408.

Figure 12:
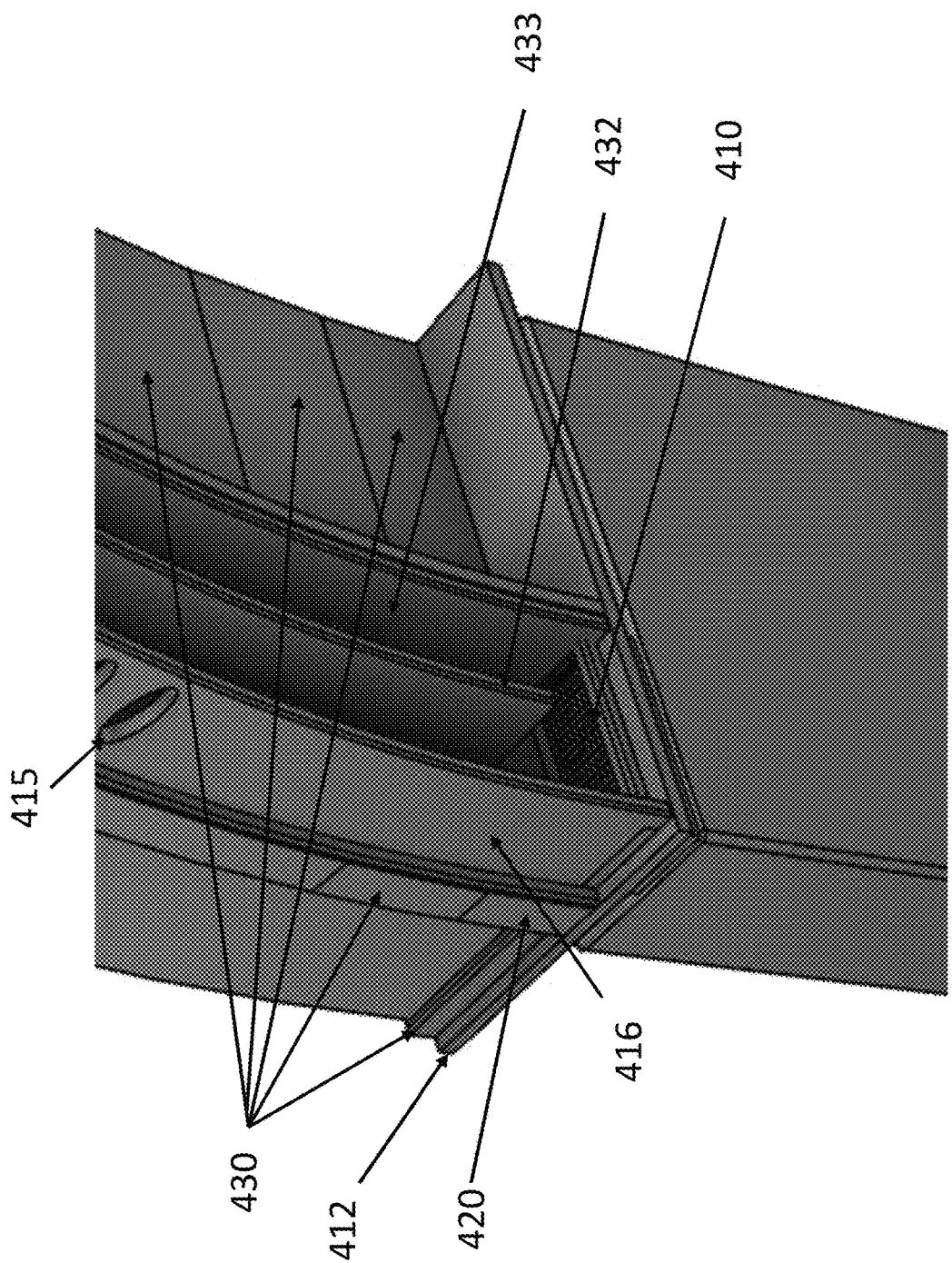
FIG. 12 illustrates a schematic diagram showing a perspective view of a bottom heat sink and a middle bottom heat sink in the wearable cooling and heating device with a Peltier device.

Further, in the preferred embodiment as illustrated in FIG. 12, the air canals 416, 417 are configured to receive a middle bottom heat sink 432 and a bottom heat sink 433, wherein the bottom heat sink 433 is the closest heat sink to the plurality of air outlets 415 and a dimension of the middle bottom heat sink 432 is smaller than that of the bottom heat sink 433 such that air can flow in between the middle bottom heat sink 432 and the bottom heat sink 433 in the air canals 416, 417.

Figure 13:
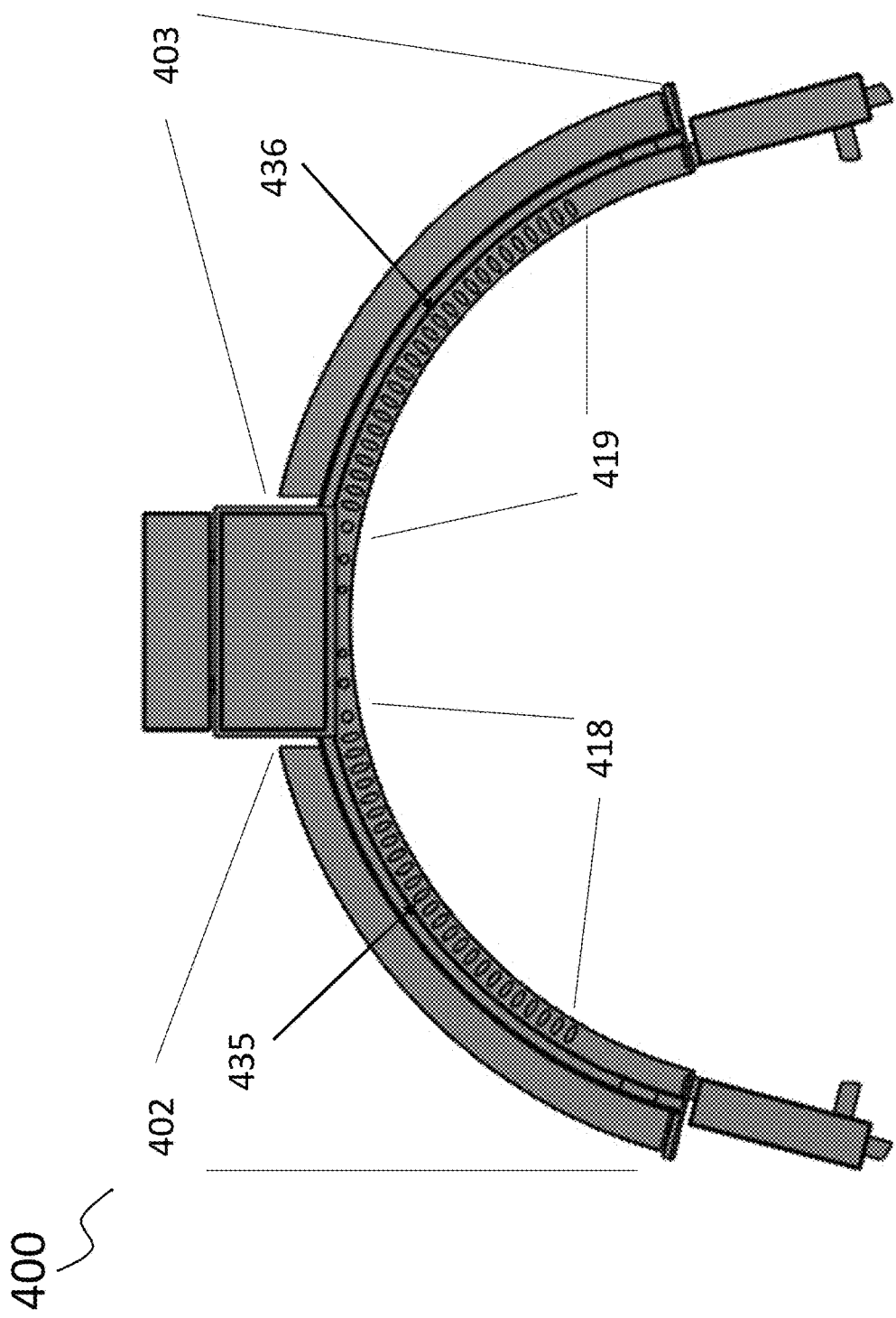
FIG. 13 illustrates a schematic diagram showing a front view of the wearable cooling and heating device with a Peltier device.

FIG. 13 illustrates a schematic diagram showing a front view of the wearable cooling and heating device with a Peltier device 400. In one embodiment, bottom heat sinks 435, 436 are aligned behind a first group of air outlets 418 and a second group of air outlets 419 located along the support arms 402, 403.

Figure 14:
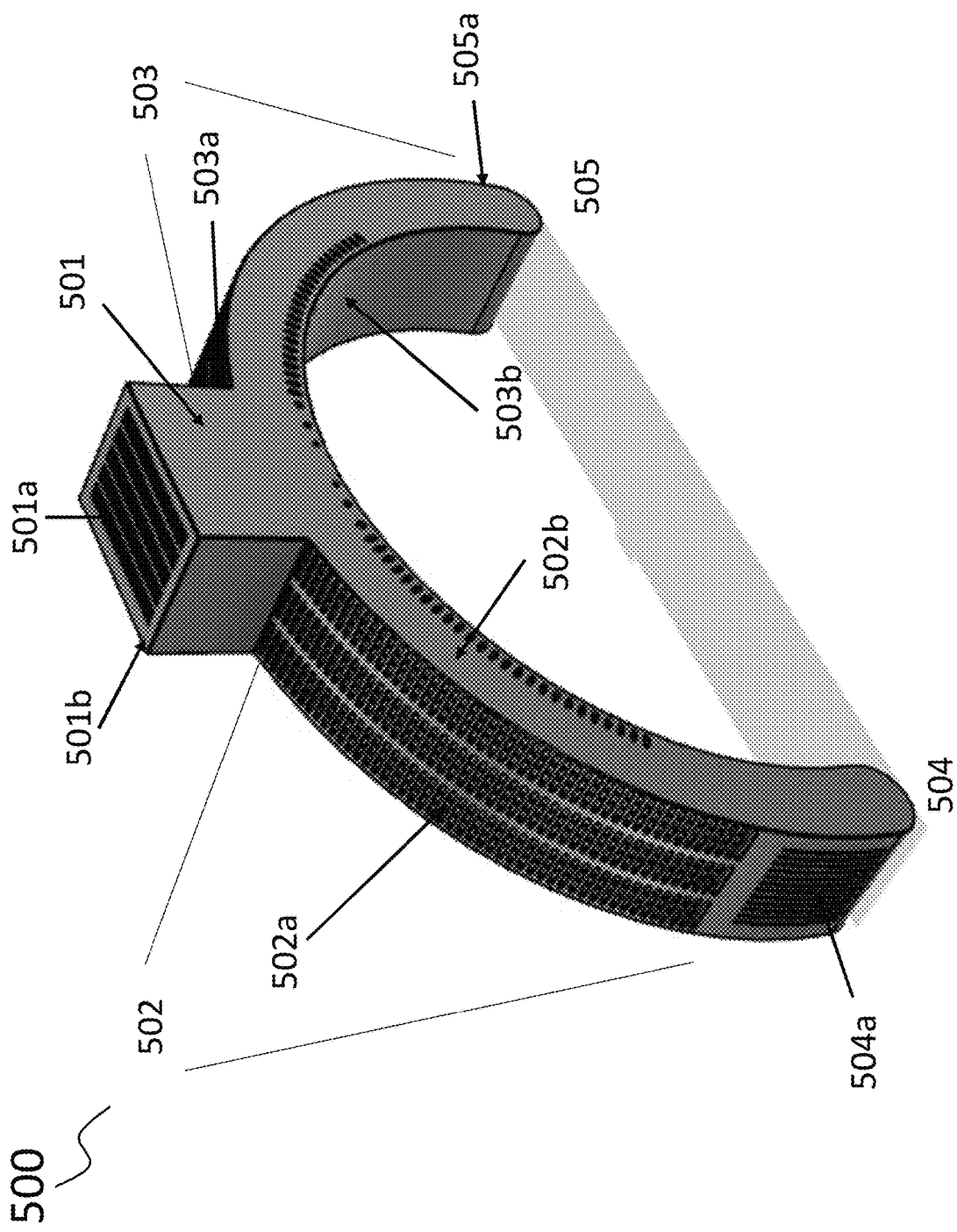
FIG. 14 illustrates a schematic diagram showing a perspective view of vents at the top and the support arms of the wearable cooling and heating device with a Peltier device.

In one embodiment as illustrated in FIG. 14, a wearable cooling and heating device 500 comprises a top vent 501a at a top 501b of a control module 501, a first heat sink vent 502a along a first top peripheral 502b of a first support arm 502, a second heat sink vent 503a along a second top peripheral 503b of a second support arm 503, a first air flow inlet 504a near a first end 504, and a second air flow inlet 505a near a second end 505.

Specifically, the top vent 501a is configured to release heat produced by the control module 501. The first and second heat sink vents 502a, 503a are slots in the first and second support arms 502, 503 respectively configured to maintain airflow in a first and second heat sinks 502b, 503b located respectively inside the first and second support arms 502, 503.

Figure 15:
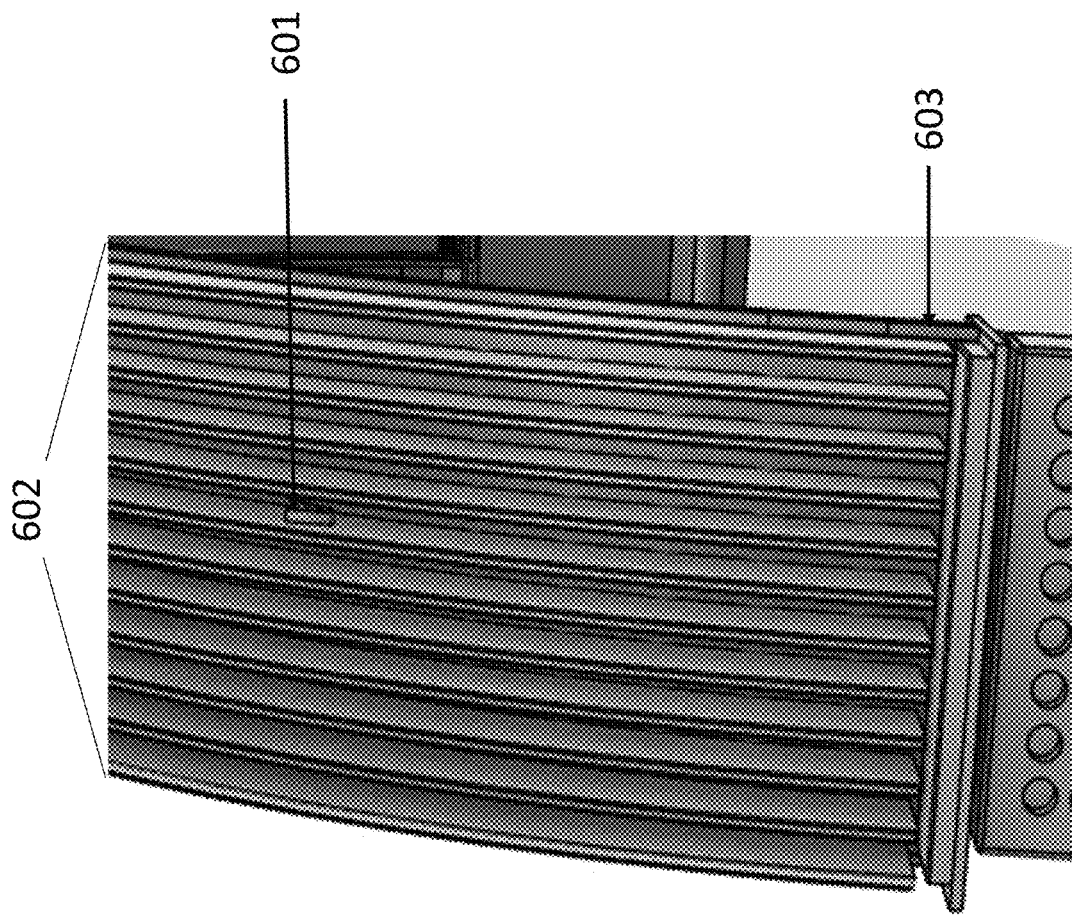
FIG. 15 illustrates a schematic diagram showing a left side view of top heat sinks and a thermistor of the wearable cooling and heating device with a Peltier device.

In one embodiment as illustrated in FIG. 15, a wearable cooling and heating device 600 utilizes natural convection and at least two thermistors 601 are provided in top heat sinks 602 and a Peltier device 603. The thermistors 601 are selected from a group consisting of negative temperature coefficient (NTC) thermistors and positive temperature coefficient (PTC) thermistors, which are directly correlated to temperature changes such that the air temperature inside the wearable cooling and heating device 600 does not exceed certain threshold. When a pre-set threshold of air temperature of the top heat sinks 602 and or the Peltier device 603 is met, the thermistors 601 shut down the Peltier device 603 to maintain an operating temperature.

Figure 15A:
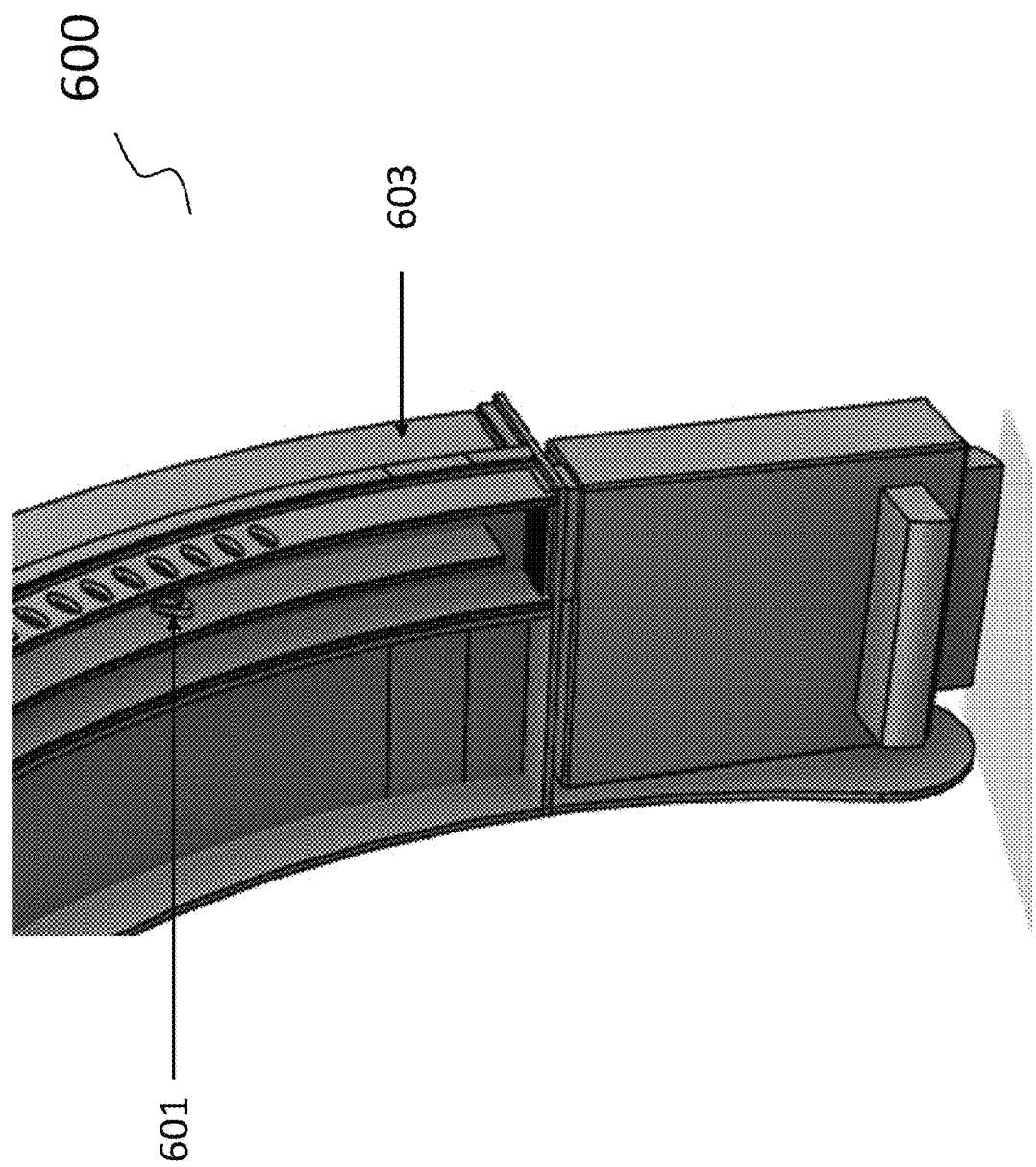
FIG. 15a illustrates a schematic diagram showing a perspective view of a thermistor at the air flow outlet.

In some embodiments as illustrated in FIG. 15a, a third thermistor can be added at the air flow outlet to measure the processed air temperature while exiting the wearable cooling and heating device in order to adjust the Peltier device surface temperature based on the readings. This will help achieve an optimizable air flow temperature.

Figure 16A:
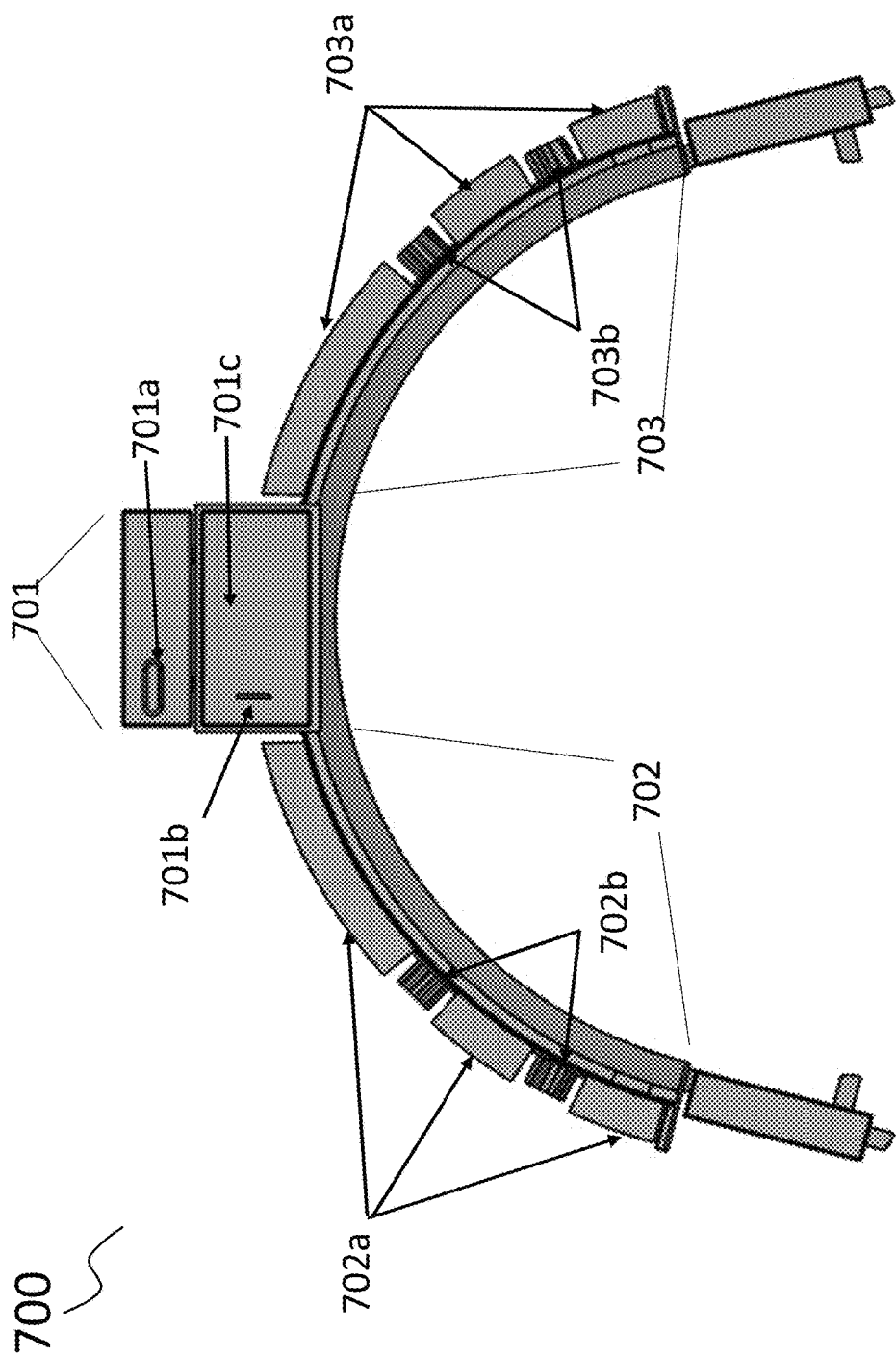
FIG. 16a illustrates a schematic diagram showing a back view of the top heat sinks and fans of the wearable cooling and heating device with a Peltier device.
Figure 16B:
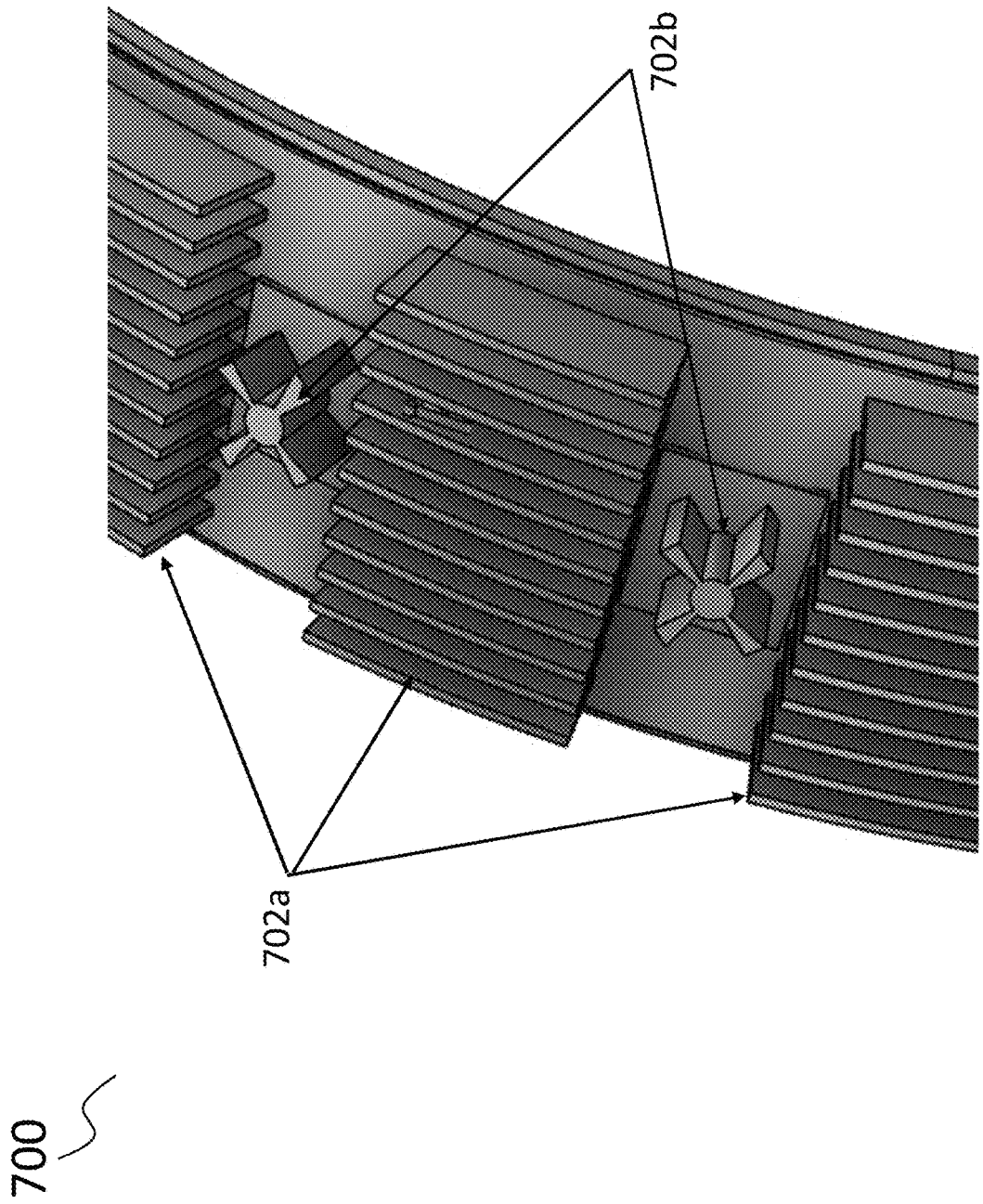
FIG. 16b illustrates a schematic diagram showing a perspective view of the top heat sinks and fans of the wearable cooling and heating device with a Peltier device.

In one embodiment as illustrated in FIGS. 16a and 16b, a wearable cooling and heating device 700 utilizes natural convection and forced air which allows top heat sinks 702a, 702b to release and absorb heat at a faster pace resulting in a higher temperature difference between surfaces of Peltier device 702c, 703c. A plurality of fans 702b, 703b are disposed at a top of a first support arm 702 and a second support arm 703 respectively. The fans 702b are distributed in between a plurality of top heat sinks 702a. The fans 703b are distributed in between a plurality of top heat sinks 703a. The configuration is designed to include a mode to generate forced air between the heat sinks 702a, 703a to increase convection.

Figure 16C:
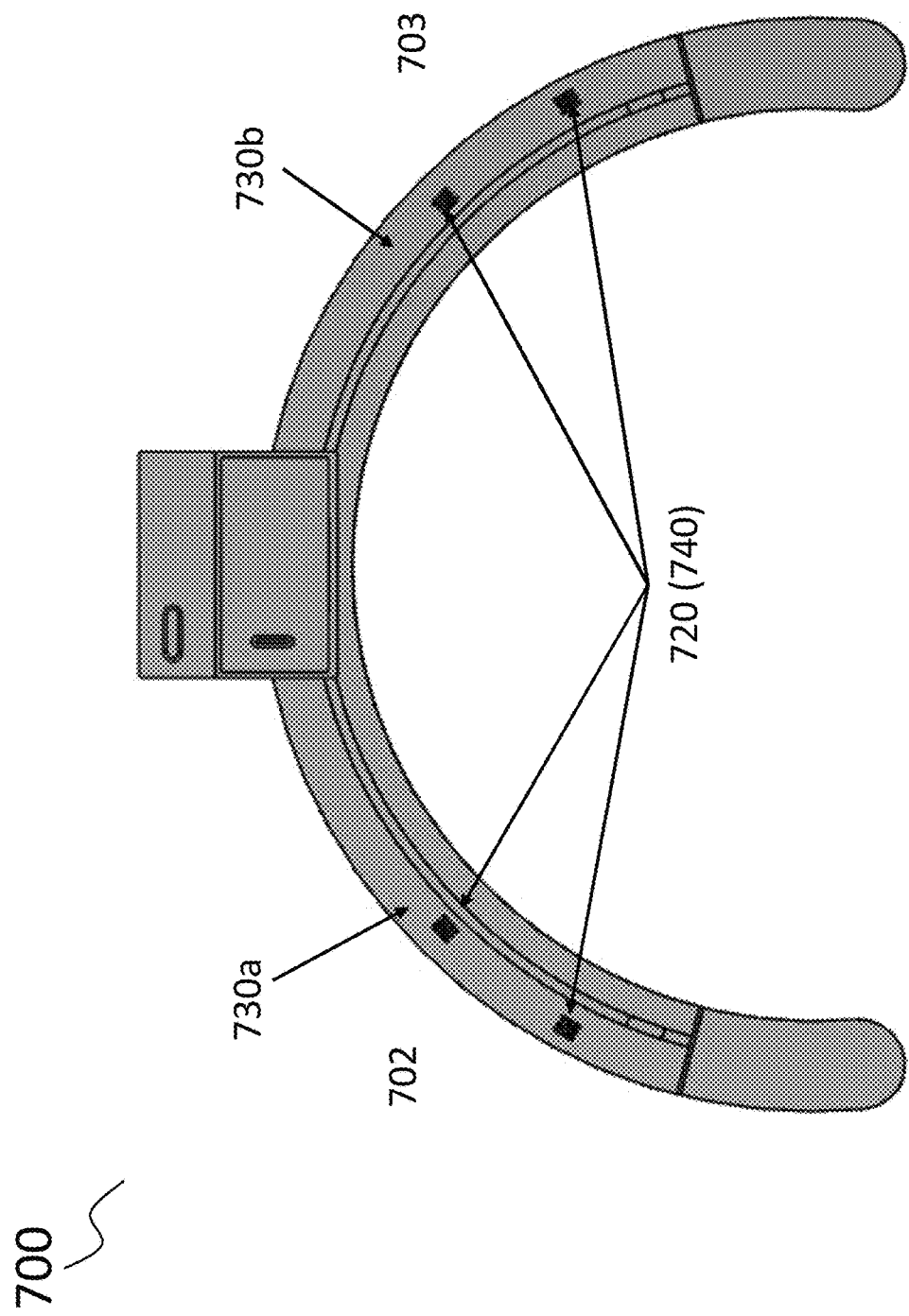
FIG. 16c illustrates a schematic diagram showing a back view of a wearable cooling and heating device with a plurality of insulation slots.

Additionally, as illustrated in FIG. 16c, the wearable cooling and heating device 700 further comprises a plurality of slots 720 in the insulation pads 730a, 730b that are aligned with a plurality of slots 740 on the first and second support arms 702, 703 which acts as air inlets for forced convection.

Figure 17A:
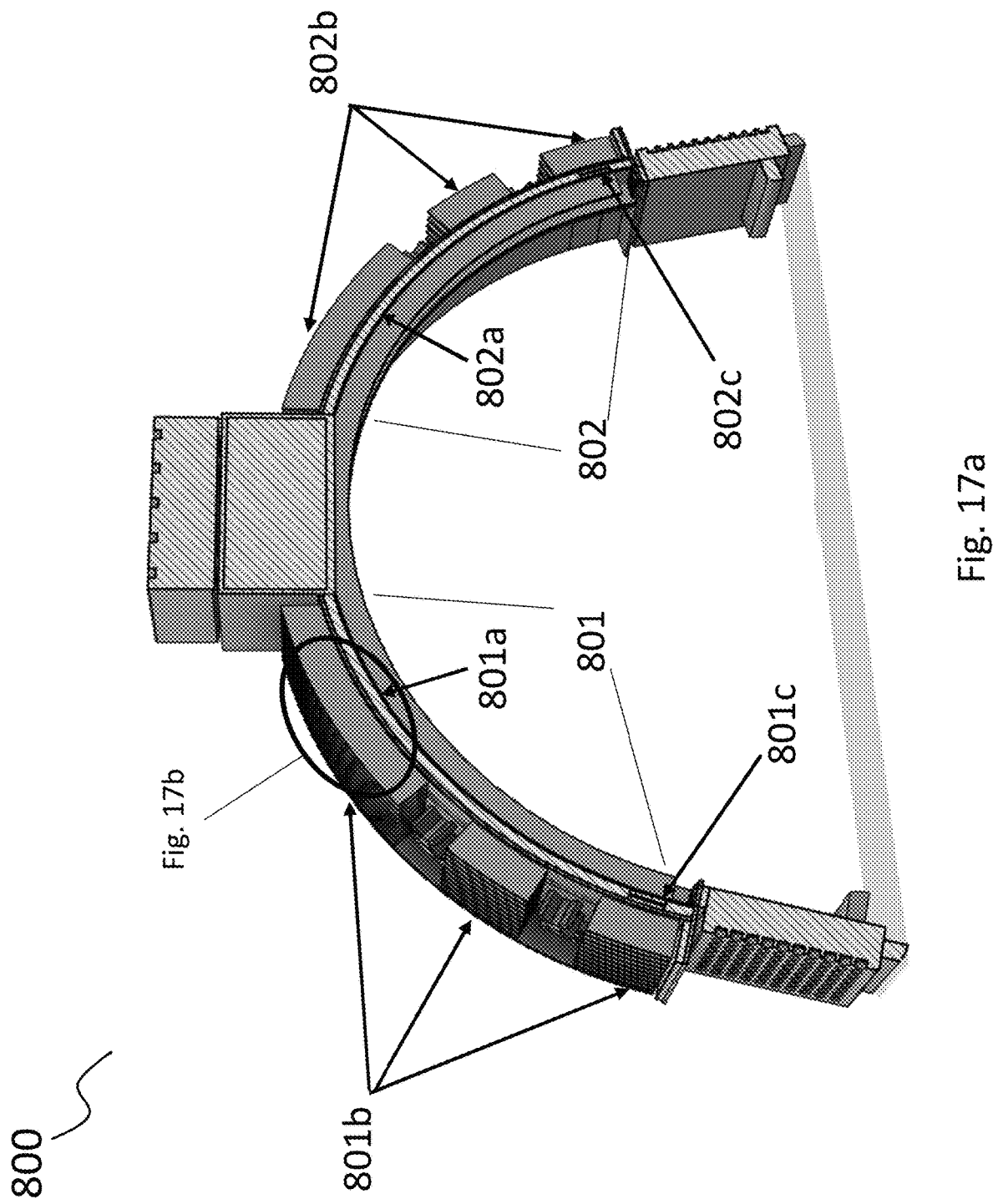
FIG. 17a illustrates a schematic diagram showing a perspective view of a wearable cooling and heating device with a Peltier device and a vapor chamber.

In one embodiment as illustrated in FIG. 17a, a wearable cooling and heating device 800 utilizes a first vapor chamber 801a and a second vapor chamber 802a which allow a plurality of top heat sinks 801b, 802b to release or absorb heat at a faster pace resulting in a higher temperature difference in a first Peltier device 801c and a second Peltier device 802c. The first vapor chamber 801a is located underneath a plurality of top heat sinks 801b in a first support arm 801. The second vapor chamber 802a is located underneath a plurality of top heat sinks 802b in a second support arm 802.

Figure 17B:
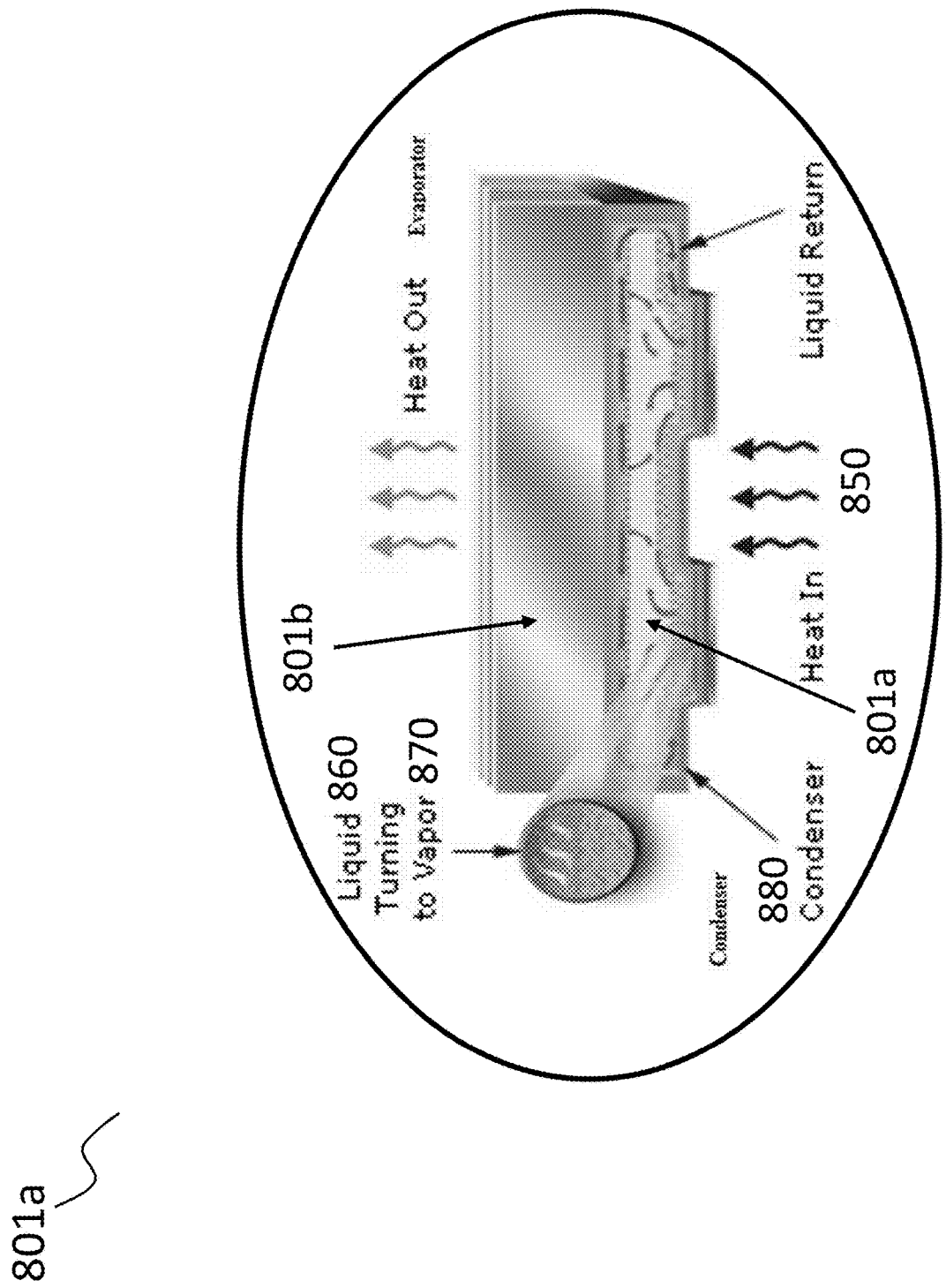
FIG. 17b illustrates a schematic diagram showing a cross-sectional view of the vapor chamber.

A cross-sectional view of the vapor chamber 801a is illustrated in FIG. 17b. Specifically, the vapor chamber 801a acts as a heat pipe to transfer heat. When hot air 850 enters the vapor chamber 801a, liquid 860 evaporates into vapor 870. The vapor 870 then travels through the vapor chamber 801a, creating an isothermal heat spreader. The vapor 870 then condenses on a condenser 880, where heat is removed by forced convection, natural convection, or liquid cooling.

Figure 18:
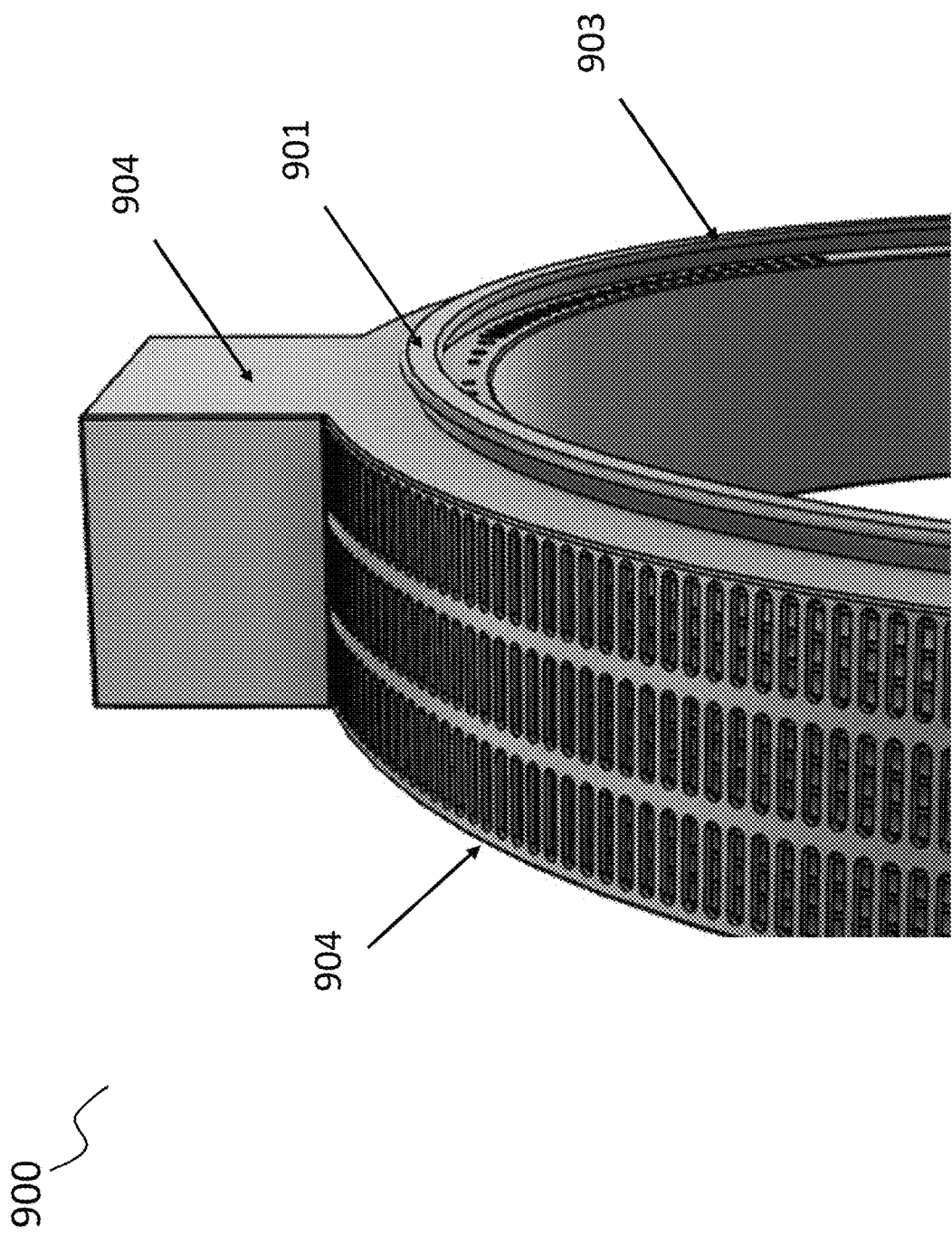
FIG. 18 illustrates a schematic diagram showing a perspective view of a cone attachment of the wearable cooling and heating device with a Peltier device.

FIG. 18 illustrates a schematic diagram showing a perspective view of a cone receiver 901 of a wearable cooling and heating device with a Peltier device 900. The cone receiver 901 is preferably extended from a front side 904 of the wearable cooling and heating device 900 along a full length of the first and second support arms 902, 903 such that a pet can wear the cooling and heating device 900 and a recovery cone around its neck at the same time.

Figure 19A:
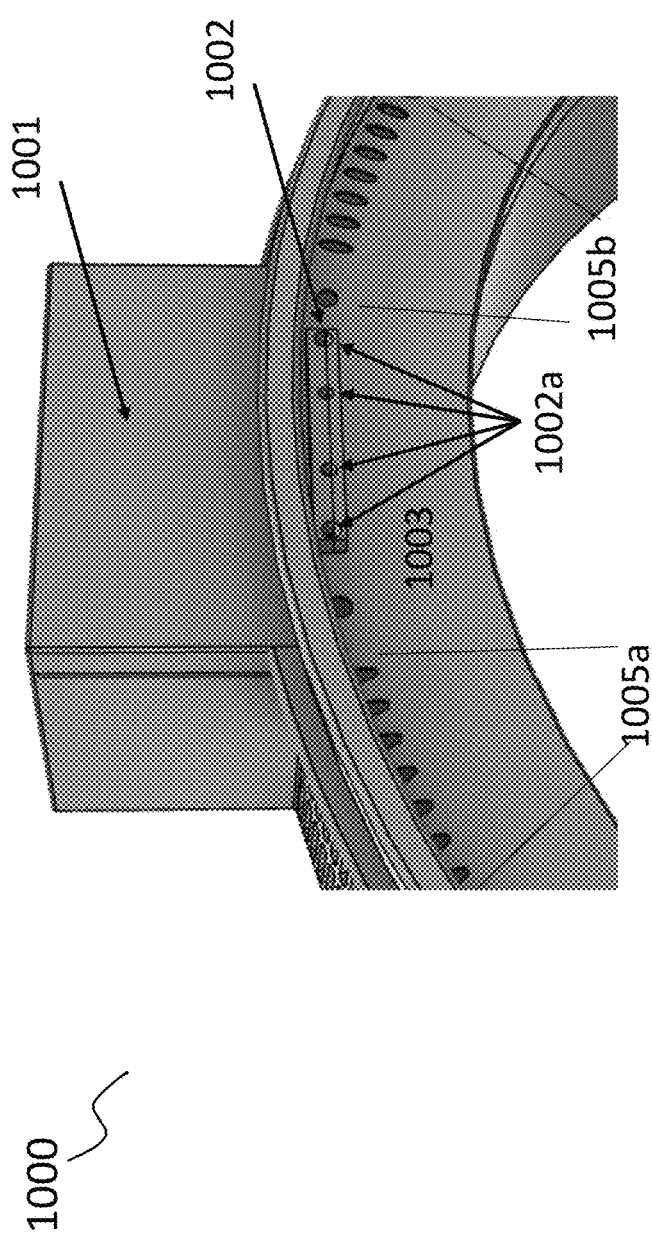
FIG. 19a illustrates a schematic diagram showing a perspective view of an aromatherapy chamber with a plurality of aromatherapy slots located under the control box of the wearable cooling and heating device with a Peltier device.
Figure 19B:
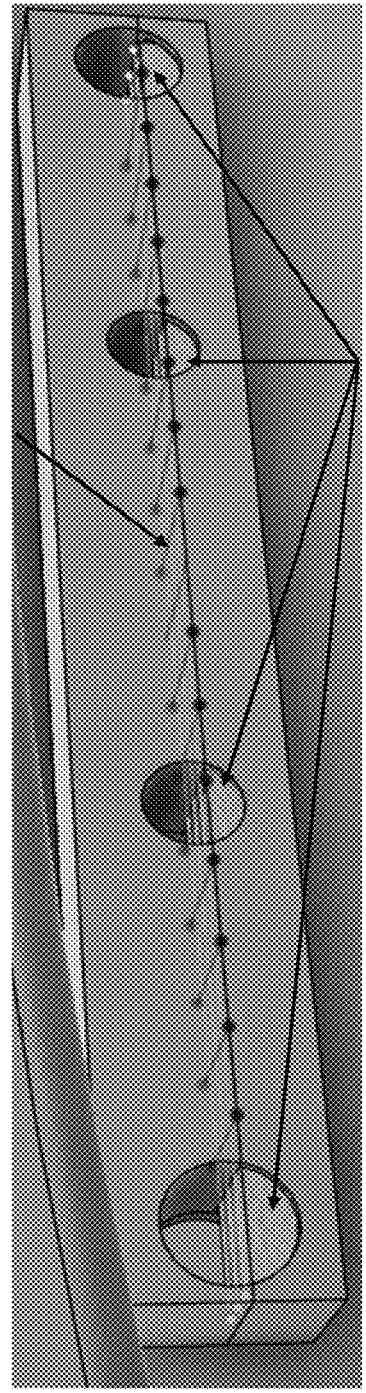
FIG. 19b illustrates a schematic diagram showing a perspective view of a mesh with diffuser sponge inside the aromatherapy chamber of the wearable cooling and heating device with a Peltier device.

In some embodiments as illustrated in FIGS. 19a and 19b, a wearable cooling and heating device 1000 comprises an aromatherapy chamber 1002 with a plurality of slots 1002a located at a mid-section 1003 of the wearable cooling and heating device 1000 underneath a control module 1001 and between a plurality of air outlets 1005a, 1005b. The aromatherapy chamber 1002 is preferably provided with a horizontal mesh 1004 disposed longitudinally across the aromatherapy chamber 1002 and a plurality of diffuser sponges 1004. The plurality of diffuser sponges 1004 releases scent into the air passing through the aromatherapy chamber 1002 to make a pet's clothing smell fresh. In addition, the use of diffuser sponges 1004 is beneficial for human and/or pet use as a stress reliever. Scents such as lavender are associated with sleep improvements. Vanilla, coconut, valerian, and ginger scents have the potential to reduce stress in pets.

Figure 20:
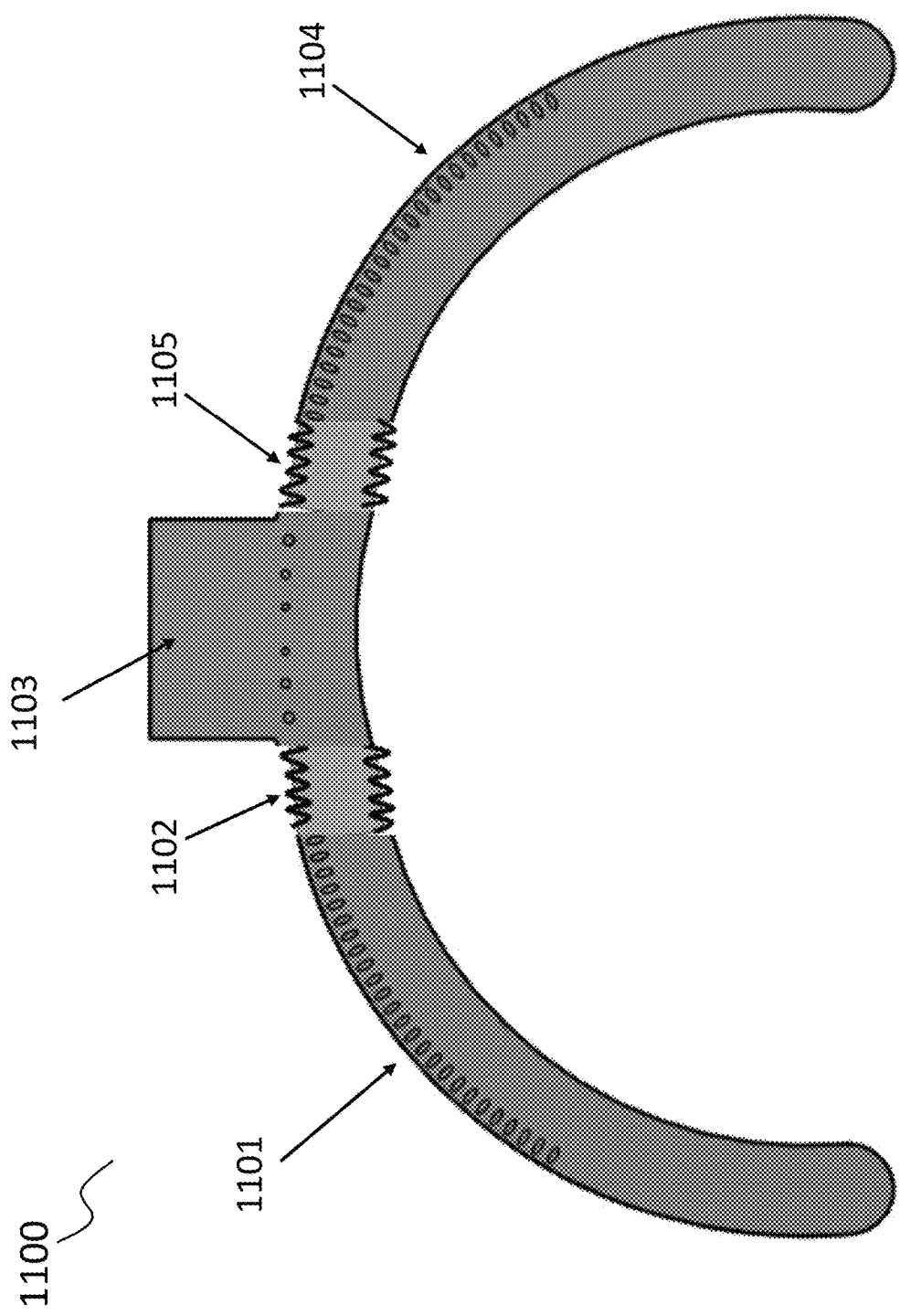
FIG. 20 illustrates a schematic diagram showing a front view of a wearable cooling and heating device with flexible connectors.

In addition, in one embodiment as illustrated in FIG. 20, a wearable cooling and heating device 1100 comprises a first flexible connector 1102 which connects a first support arm 1101 and a control module 1103, and a second flexible connector 1105 which connects a second support arm 1104 and the control module 1103. The first and second flexible connectors 1102, 1105 are preferably made of bendable plastic composite material or durable fabric to allow for flexibility to fit various sizes of a body part, harness, stroller, clothing, or handheld devices.

Figure 21:
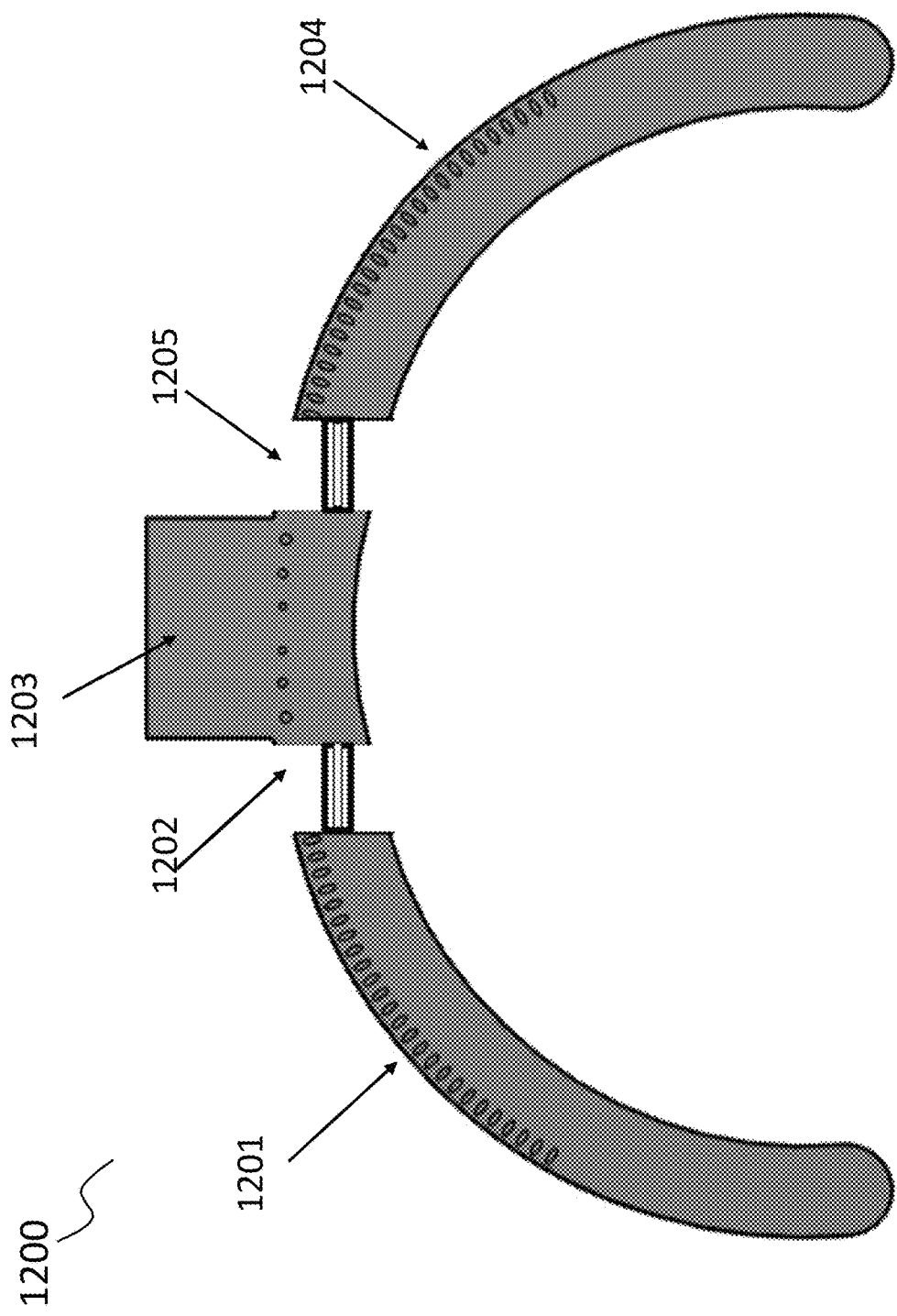
FIG. 21 illustrates a schematic diagram showing a front view of a wearable cooling and heating device with retractable connectors.

In some other embodiments as illustrated in FIG. 21, a wearable cooling and heating device 1200 comprises a first retractable connector 1202 which connects a first support arm 1201 and a control module 1203, and a second retractable connector 1205 which connects a second support arm 1204 and the control module 1203. The first and second retractable connectors 1202, 1205 can be extended and retracted to accommodate different needs.

Figures 22A, 22B:
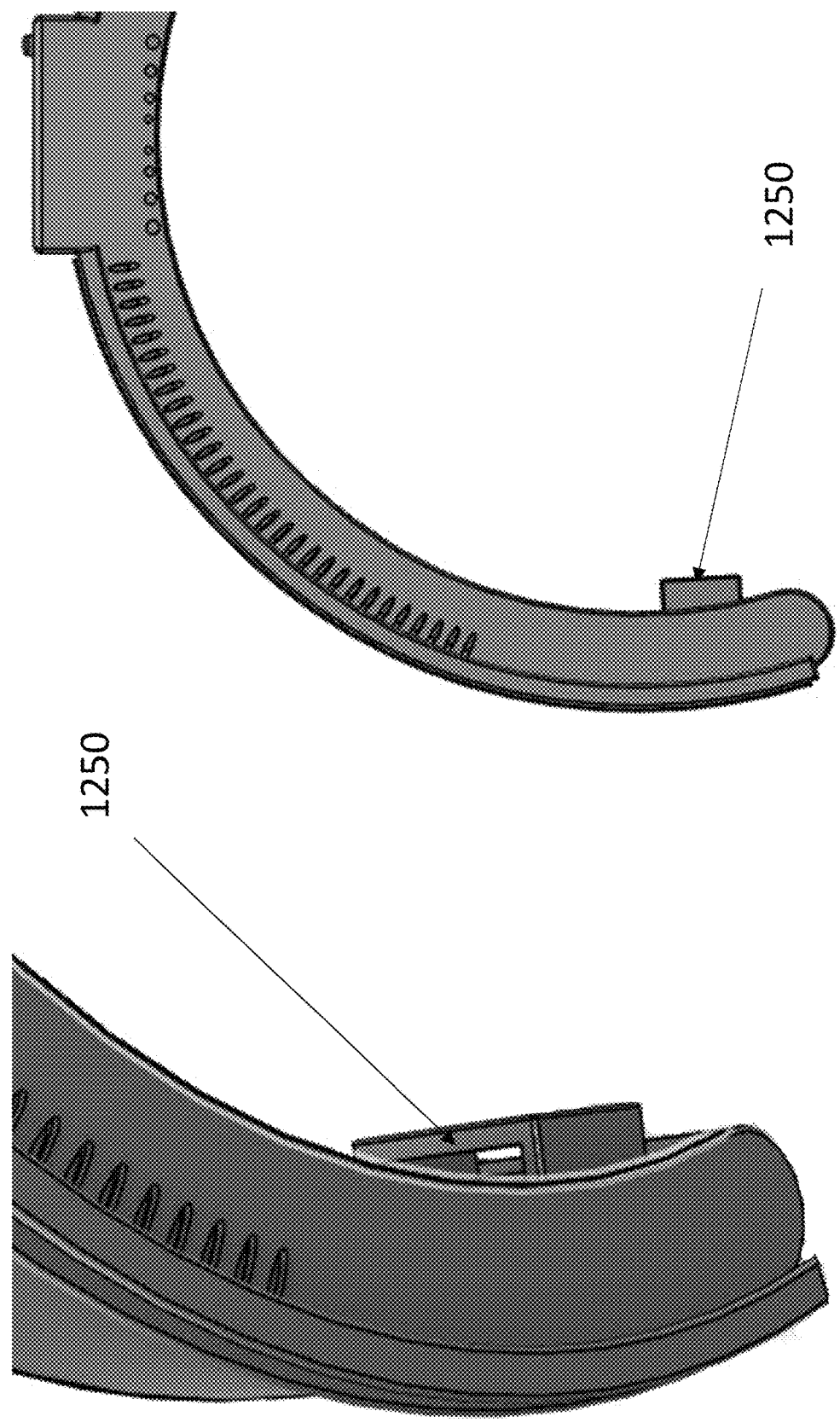
FIGS. 22a-22b illustrate schematic diagrams showing a close-up side perspective view and a side view of a wearable cooling and heating device with an optional slot for a pet harness.

FIGS. 22a-22b illustrate an alternative embodiment of the wearable cooling and heating device, wherein a slot 1250 is provided to an inner side of the device to allow a pet collar or harness to be placed through the slot 1250 thereby enabling the heating and cooling device to rest on the top of a pet.

As shown herein, a portable and wearable cooling and heating device configured to regulate temperature for comfort by blowing cool or warm air that is easily transferrable, light weight, and flexible is disclosed. The wearable cooling and heating device comprises a first support arm, a second support arm, and a control module that is preferably battery powered configured to control the speed of air flow. The first and second support arm each further comprises an air canal with a plurality of air outlets, temperature packs, insulation pads, a housing configured to receive an air flow supplier, an air flow supplier nozzle that directs and enhances the air flow, an air flow barrier that prevents air from reentering the air flow supplier. In some embodiments, the first and second support arms of the wearable cooling and heating device are further provided with at least one Peltier device to optimize the air temperature, a plurality of fans to generate forced air, a plurality of air outlets along the length of the support arms, heat sinks inside the support arms, thermistors to monitor the temperature inside the air canals. Other embodiments also include an aromatherapy chamber designed to receive a number of diffuser pads/sponges that can release different scent into the air.

What is claimed is:

1. A portable and wearable cooling and heating device configured to regulate temperature, the device comprising:
    a first support arm with a first distal end and a first proximal end;
    a second support arm with a second distal end and a second proximal end;
    a control module;
    wherein the first proximal end of the first support arm and the second proximal end of the second support arm are connected such that the portable and wearable cooling and heating device possesses a continuous curvature;
    wherein the control module further comprises:
        a power source; and
        a control panel with a control switch;
    wherein a first housing is located at a first distal end of the first support arm and a second housing is located at a second distal end of the second support arm;
    wherein the first and second housings each further comprises:
        an air flow supplier;
        an air flow supplier nozzle configured to direct and enhance air flow; and
        an air flow barrier configured to prevent the air flow from reentering the air flow supplier;
    wherein the first and second support arms each comprises:
        an elongated and curved air canal connected to the air flow supplier nozzle that is extended along the continuous curvature;
        a plurality of air outlets located along a length of the continuous curvature in the elongated and curved air canal; and
        a plurality of insulation pads enclosed by the first and second support arms;
    wherein the first and second support arms and the control module are connected by a first and a second retractable connectors such that a circumference of the device is adjustable to accommodate different needs.

2. The portable and wearable cooling and heating device according to claim 1, wherein the first and second support arms each comprises at least one temperature pack inside the elongated and curved air canal that is enclosed by the plurality of insulation pads, wherein the temperature pack is configured to warm and cool the air flow directed by the air flow supplier nozzle.

3. The portable and wearable cooling and heating device according to claim 1, wherein the control module further comprises a charging port configured to charge the power source.

4. The portable and wearable cooling and heating device according to claim 1, wherein the first and second support arms each further comprises an alignment notch near the first and second proximal ends respectively to ensure proper insertion of at least one temperature pack in the first and second support arms.

5. The portable and wearable cooling and heating device according to claim 1, wherein a canal exit is located at the first and second proximal ends respectively to let out any residue air from the first and second curved air canals.

6. The portable and wearable cooling and heating device according to claim 1, wherein a front center air barrier is attached underneath the control module.

7. The portable and wearable cooling and heating device according to claim 1, wherein the first and second support arms each comprises a removable back cover for easy access and replacement of at least one temperature pack.

8. The portable and wearable cooling and heating device according to claim 1, wherein a first air inlet is disposed outwardly from the continuous curvature at the first distal end, and a second air inlet is disposed outwardly from the continuous curvature at the second distal end.

9. The portable and wearable cooling and heating device according to claim 1, wherein the control module further comprises a vent cover at a top of the control module to release heat produced by the control module.

10. The portable and wearable cooling and heating device according to claim 1, wherein a first cone receiver is disposed at a front side of the first support arm from the first distal end to the first proximal end, and a second cone receiver is disposed a front side of the second support arm from the second distal end to the second proximal end.

11. The portable and wearable cooling and heating device according to claim 1, wherein the device further comprises at least one Peltier device located adjacent to the air flow barrier and the air flow supplier nozzle to manipulate air temperature.

12. The portable and wearable cooling and heating device according to claim 1, wherein the first and second support arms each comprises a middle bottom heat sink and a bottom heat sink; and wherein the bottom heat sink is aligned with the plurality of air outlets; and wherein a dimension of the middle bottom heat sink is smaller than a dimension of the bottom heat sink such that air flows between the middle bottom heat sink and the bottom heat sink in the elongated and curved air canal.

13. The portable and wearable cooling and heating device according to claim 1, wherein the device further comprises:
    a top vent configured to release heat from the control module;
    a first heat sink vent located along a first top peripheral of the first support arm;
    a second heat sink vent located along a second top peripheral of the second support arm;

a first air flow inlet at the first distal end; and a second air flow inlet at the second distal end.

14. The portable and wearable cooling and heating device according to claim 11, wherein the device further comprises at least one thermistor located in a top heat sink, wherein the thermistor is configured to maintain an air temperature inside the device.

15. The portable and wearable cooling and heating device according to claim 11, wherein the device further comprises at least one thermistor located on the at least one Peltier device configured to control the at least one Peltier device if a pre-set temperature threshold is exceeded.

16. The portable and wearable cooling and heating device according to claim 14, wherein the device further comprises a plurality of fans disposed at a first top surface of the first support arm and a second top surface of the second support arm to generate forced air to increase natural convection.

17. The portable and wearable cooling and heating device according to claim 1, wherein the plurality of insulation pads comprises a plurality of slots that are aligned with a plurality of slots located on the first support arm and the second support arm.

18. The portable and wearable cooling and heating device according to claim 16, wherein the first support arm comprises a first vapor chamber and the second support arm comprises a second vapor chamber; wherein the first and the second vapor chambers are disposed underneath the top heat sink.

19. The portable and wearable cooling and heating device according to claim 11, wherein the device comprises an aromatherapy chamber with a plurality of slots located at a mid-section of the device underneath the control module and between the plurality of air outlets; and wherein the aromatherapy chamber is provided with a horizontal mesh disposed longitudinally inside the aromatherapy chamber and a plurality of diffuser sponges.

* * * * *